United States Patent
Jacobsen et al.

(10) Patent No.: US 12,310,676 B2
(45) Date of Patent: May 27, 2025

(54) NAVIGATION AT ULTRA LOW TO HIGH FREQUENCIES

(71) Applicant: Medtronic Navigation, Inc., Louisville, CO (US)

(72) Inventors: Bradley W. Jacobsen, Erie, CO (US); Victor D. Snyder, Erie, CO (US); Andrew J. Wald, Fort Worth, TX (US)

(73) Assignee: Medtronic Navigation, Inc., Louisville, CO (US)

( * ) Notice: Subject to any disclaimer, the term of this patent is extended or adjusted under 35 U.S.C. 154(b) by 141 days.

(21) Appl. No.: 17/992,604

(22) Filed: Nov. 22, 2022

(65) Prior Publication Data

US 2024/0164843 A1 May 23, 2024

(51) Int. Cl.
A61B 34/20 (2016.01)
A61B 5/06 (2006.01)

(52) U.S. Cl.
CPC ............. *A61B 34/20* (2016.02); *A61B 5/062* (2013.01); *A61B 2034/2051* (2016.02)

(58) Field of Classification Search
CPC .. A61B 34/20; A61B 5/062; A61B 2034/2051
See application file for complete search history.

(56) References Cited

U.S. PATENT DOCUMENTS

| | | |
|---|---|---|
| 2004/0207389 A1 | 10/2004 | Nieminen et al. |
| 2008/0162074 A1* | 7/2008 | Schneider ............ A61B 34/20 702/150 |
| 2009/0082989 A1* | 3/2009 | Zuhars ............... A61B 34/20 702/150 |
| 2011/0004430 A1* | 1/2011 | Nieminen ........... A61B 34/20 702/66 |
| 2011/0148714 A1 | 6/2011 | Schantz et al. |
| 2014/0187915 A1* | 7/2014 | Yaroshenko ........ A61B 34/20 600/424 |
| 2019/0328272 A1 | 10/2019 | Ronen et al. |
| 2022/0296310 A1 | 9/2022 | Jacobsen et al. |

OTHER PUBLICATIONS

International Search Report and Written Opinion for International (PCT) Patent Application No. PCT/IB2023/061734, dated Feb. 22, 2024, 15 pages.

* cited by examiner

*Primary Examiner* — Joel Lamprecht
*Assistant Examiner* — Nyrobi Celestine
(74) *Attorney, Agent, or Firm* — Sheridan Ross P.C.

(57) ABSTRACT

A system and method include transmitting a signal according to a set of frequencies. A frequency range associated with the set of frequencies is from about 300 Hz to about 30 MHz. The system and method include sensing an electromagnetic field based on transmitting the signal according to the set of frequencies and determining a distortion in association with sensing the electromagnetic field. The system and method include identifying frequencies at which the magnitude of the distortion is less than the threshold value. The system and method include transmitting the signal according to one or more of the identified frequencies and providing navigation information associated with an environment in response to transmitting the signal.

30 Claims, 8 Drawing Sheets

NAVIGATION AT ULTRA LOW TO HIGH FREQUENCIES

FIELD OF INVENTION

The present disclosure is generally directed to navigation systems, and relates more particularly to navigation at ultra low to high frequencies.

BACKGROUND

Navigation systems may assist a surgeon or other medical provider in performing a surgical procedure. Some navigation systems may utilize an electromagnetic field in association with tracking objects in association with the surgical procedure. Distortions impacting the electromagnetic field may reduce the effectiveness of the navigation system.

BRIEF SUMMARY

Example aspects of the present disclosure include:

A system including: a processor; and a memory storing instructions thereon that, when executed by the processor, cause the processor to: transmit a signal according to a set of frequencies, wherein a frequency range associated with the set of frequencies is from about 300 Hz to about 30 MHz; determine a distortion in association with an electromagnetic field sensed at a tracking device, wherein the distortion is determined with respect to the set of frequencies; identify, from among the set of frequencies, a set of second frequencies at which the magnitude of the distortion is less than the threshold value; transmit the signal according to one or more frequencies of the set of second frequencies; and provide navigation information associated with an environment and the tracking device in response to transmitting the signal according to the one or more frequencies, wherein the navigation information includes pose information of the tracking device.

Any of the aspects herein, wherein the instructions are further executable by the processor to: configure a model in association with compensating for the distortion with respect to at least one frequency of the one or more frequencies, wherein providing the navigation information is based on compensating for the distortion using the model.

Any of the aspects herein, wherein compensating for the distortion using the model includes reducing the magnitude associated with the distortion.

Any of the aspects herein, wherein the at least one frequency is greater than a threshold frequency included among the one or more frequencies.

Any of the aspects herein, wherein: transmitting the signal according to the one or more frequencies includes incrementally increasing or decreasing a frequency associated with transmitting the signal, from a first boundary frequency to a second boundary frequency included in the set of second frequencies.

Any of the aspects herein, wherein: the first boundary frequency is identified based on a comparison of the threshold value and a first distortion magnitude associated with transmitting the signal according to the first boundary frequency; and the second boundary frequency is identified based on a comparison of the threshold value and a second distortion magnitude associated with transmitting the signal according to the second boundary frequency.

Any of the aspects herein, wherein determining the distortion is based on at least one of: a magnetic permeability associated with one or more objects in the environment; and a relative permeability associated with the one or more objects in the environment.

Any of the aspects herein, further including a set of transmission coils, wherein the instructions are further executable by the processor to: transmit the signal from a first transmission coil of the set of transmission coils; and transmit the signal or a second signal according to one or more second frequencies of the set of frequencies, from a second transmission coil of the set of transmission coils; and provide the navigation information associated with the environment and the tracking device in response to transmitting the signal or the second signal according to the one or more second frequencies.

Any of the aspects herein, wherein the distortion includes at least one of: a conductive distortion associated with one or more objects in the environment; and a magnetic distortion associated with the one or more objects in the environment.

Any of the aspects herein, wherein the distortion is associated with one or more objects included in the environment, the one or more objects including at least one of: one or more ferromagnetic objects: and one or more non-ferromagnetic objects.

A method including: transmitting a signal according to a set of frequencies, wherein a frequency range associated with the set of frequencies is from about 300 Hz to about 30 MHz; sensing an electromagnetic field based on transmitting the signal according to the set of frequencies; determining a distortion with respect to the set of frequencies in association with sensing the electromagnetic field; identifying, from among the set of frequencies, a set of second frequencies at which the magnitude of the distortion is less than the threshold value; transmitting the signal according to one or more frequencies of the set of second frequencies; and providing navigation information associated with an environment and the tracking device in response to transmitting the signal according to the one or more frequencies, wherein the navigation information includes pose information of the tracking device.

Any of the aspects herein, further including: configuring a model in association with the compensating for the distortion with respect to at least one frequency of the one or more frequencies, wherein providing the navigation information is based on compensating for the distortion using the model.

Any of the aspects herein, wherein compensating for the distortion using the model includes reducing a magnitude associated with the distortion.

Any of the aspects herein, wherein the at least one frequency includes a relatively high frequency included among the one or more frequencies.

Any of the aspects herein, wherein: transmitting the signal according to the one or more frequencies includes incrementally increasing or decreasing a frequency associated with transmitting the signal, from a first boundary frequency to a second boundary frequency included in the set of second frequencies.

Any of the aspects herein, further including: identifying the first boundary frequency based on a comparison of the threshold value and a first distortion magnitude associated with transmitting the signal according to the first boundary frequency; and identifying the second boundary frequency based on a comparison of the threshold value and a second distortion magnitude associated with transmitting the signal according to the second boundary frequency.

Any of the aspects herein, wherein determining the distortion is based on at least one of: a magnetic permeability associated with one or more objects in the environment; and a relative permeability associated with the one or more objects in the environment.

Any of the aspects herein, further including: transmitting the signal from a first transmission coil of a set of transmission coils; transmitting the signal or a second signal according to one or more second frequencies of the set of frequencies, from a second transmission coil of the set of transmission coils; and providing the navigation information associated with the environment and the tracking device in response to transmitting the signal or the second signal according to the one or more second frequencies.

Any of the aspects herein, wherein determining the distortion includes determining at least one of: a conductive distortion associated with one or more objects in the environment; and a magnetic distortion associated with the one or more objects in the environment.

Any of the aspects herein, wherein the distortion is associated with one or more objects included in the environment, the one or more objects including at least one of: one or more ferromagnetic objects: and one or more non-ferromagnetic objects.

A system including: a transmission device that is configured to transmit a signal according to a set of frequencies from about 300 Hz to about 30 MHz; a tracking device; a processor; and a memory storing data thereon that, when processed by the processor, cause the processor to: determine a distortion in association with an electromagnetic field sensed at the tracking device, wherein the distortion is determined with respect to the set of frequencies; identify, from among the set of frequencies, a set of second frequencies at which the magnitude of the distortion is less than the threshold value; transmit the signal using the transmission device according to one or more frequencies of the set of second frequencies; and provide navigation information associated with an environment and the tracking device in response to transmitting the signal according to the one or more frequencies, wherein the navigation information includes pose information of the tracking device.

Any of the aspects herein, wherein the data is further executable by the processor to: configure a model in association with compensating for the distortion with respect to at least one frequency of the one or more frequencies, wherein providing the navigation information is based on applying the model.

Any of the aspects herein, wherein: transmitting the signal according to the one or more frequencies includes incrementally increasing or decreasing a frequency associated with transmitting the signal, from a first boundary frequency to a second boundary frequency included in the set of second frequencies.

Any of the aspects herein, wherein: the first boundary frequency is identified based on a comparison of the threshold value and a first distortion magnitude associated with transmitting the signal according to the first boundary frequency; and the second boundary frequency is identified based on a comparison of the threshold value and a second distortion magnitude associated with transmitting the signal according to the second boundary frequency.

Any of the aspects herein, wherein determining the distortion is based on at least one of: a magnetic permeability associated with one or more objects in the environment; and a relative permeability associated with the one or more objects in the environment.

Any of the aspects herein, wherein the transmission device includes a set of transmission coils, and the data is further executable by the processor to: transmit the signal from a first transmission coil of the set of transmission coils; transmit the signal or a second signal according to one or more second frequencies of the set of frequencies, from a second transmission coil of the set of transmission coils; and provide the navigation information associated with the environment and the tracking device in response to transmitting the signal or the second signal according to the one or more second frequencies.

Any of the aspects herein, wherein the distortion includes at least one of: a conductive distortion associated with one or more objects in the environment; and a magnetic distortion associated with the one or more objects in the environment.

Any of the aspects herein, wherein the distortion is associated with one or more objects included in the environment, the one or more objects including at least one of: one or more ferromagnetic objects: and one or more non-ferromagnetic objects.

A system, including: navigation circuitry to provide navigation information associated with an environment by: transmitting a signal according to a set of frequencies, wherein a frequency range associated with the set of frequencies is from about 300 Hz to about 30 MHz; sensing an electromagnetic field based on transmitting the signal according to the set of frequencies; determining a distortion in association with sensing the electromagnetic field, wherein the distortion is determined with respect to the set of frequencies; identifying, from among the set of frequencies, a set of second frequencies at which the magnitude of the distortion is less than the threshold value; transmitting the signal according to one or more frequencies of the set of second frequencies; and providing navigation information associated with an environment in response to transmitting the signal according to the one or more frequencies, wherein the navigation information includes pose information of one or more objects in the environment.

A non-transitory computer readable medium including instructions, which when executed by a processor: transmits a signal according to a set of frequencies, wherein a frequency range associated with the set of frequencies is from about 300 Hz to about 30 MHz; determines a distortion in association with an electromagnetic field sensed at a tracking device, wherein the distortion is determined with respect to the set of frequencies; identifies, from among the set of frequencies, a set of second frequencies at which a magnitude of the distortion is less than the threshold value; transmits the signal according to one or more frequencies of the set of second frequencies; and provides navigation information associated with an environment and the tracking device in response to transmitting the signal according to the one or more frequencies, wherein the navigation information includes pose information of the tracking device.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/implementations in combination with any one or more other aspects/features/implementations.

Use of any one or more of the aspects or features as disclosed herein.

It is to be appreciated that any feature described herein can be claimed in combination with any other feature(s) as described herein, regardless of whether the features come from the same described implementation.

The details of one or more aspects of the disclosure are set forth in the accompanying drawings and the description below. Other features, objects, and advantages of the techniques described in this disclosure will be apparent from the description and drawings, and from the claims.

The preceding is a simplified summary of the disclosure to provide an understanding of some aspects of the disclosure. This summary is neither an extensive nor exhaustive overview of the disclosure and its various aspects, implementations, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, implementations, and configurations of the disclosure are possible utilizing, alone or in combination, one or more of the features set forth above or described in detail below.

Numerous additional features and advantages of the present disclosure will become apparent to those skilled in the art upon consideration of the implementation descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, implementations, and configurations of the disclosure, as illustrated by the drawings referenced below.

DETAILED DESCRIPTION

Figure 1A:
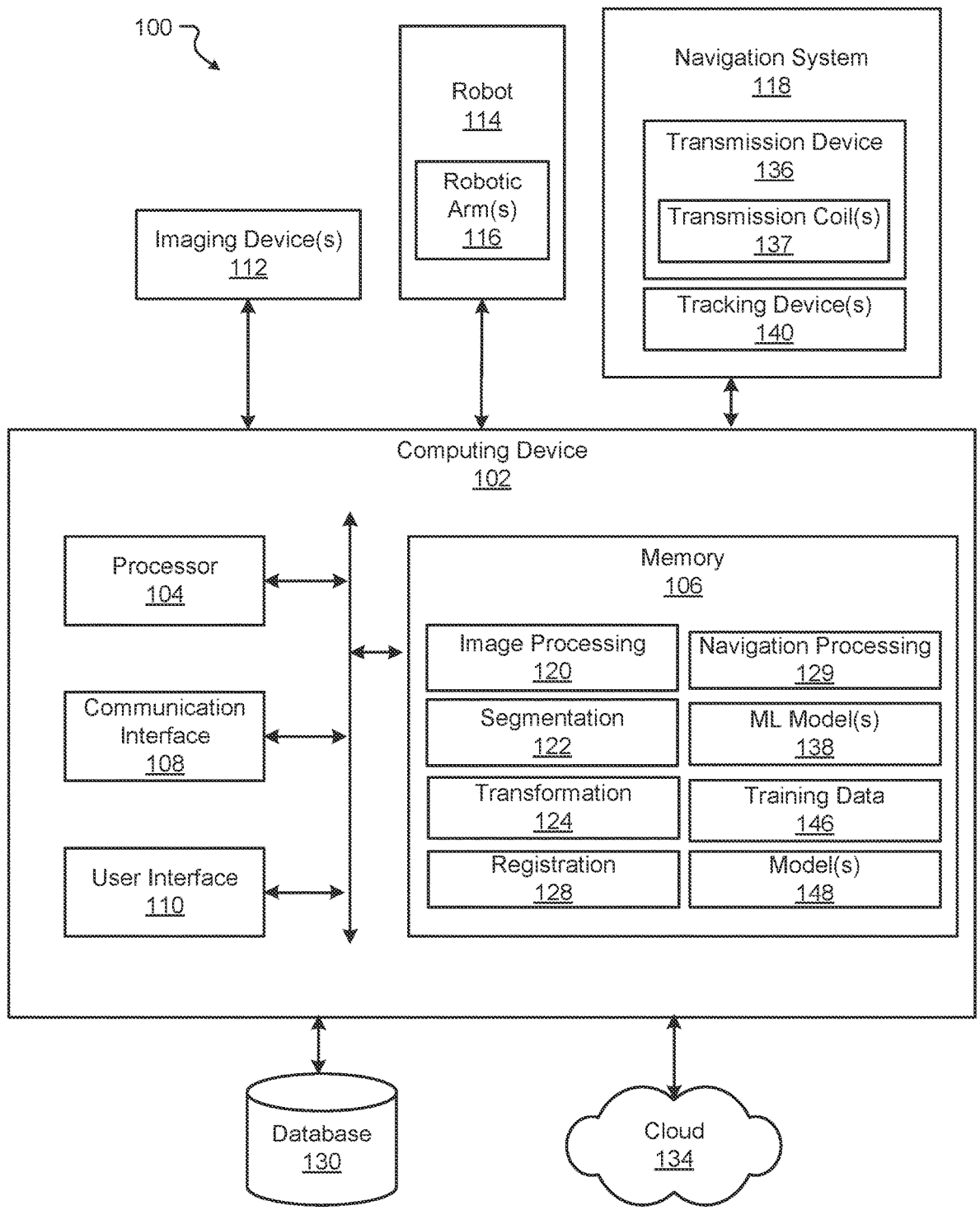
FIGS. 1A and 1B illustrate examples of a system in accordance with aspects of the present disclosure.

It should be understood that various aspects disclosed herein may be combined in different combinations than the combinations specifically presented in the description and accompanying drawings. It should also be understood that, depending on the example or implementation, certain acts or events of any of the processes or methods described herein may be performed in a different sequence, and/or may be added, merged, or left out altogether (e.g., all described acts or events may not be necessary to carry out the disclosed techniques according to different implementations of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can support store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any implementations of the disclosure are explained in detail, it is to be understood that the disclosure is not limited in its application to the details of construction and the arrangement of components set forth in the following description or illustrated in the drawings. The disclosure is capable of other implementations and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

In some navigation systems for various procedures, such as surgical procedures, assembling procedures, and the like, an instrument or object may be tracked by measuring an effect of an electromagnetic field on a sensor coil. The sensor coil may include a conductive material that is placed within a magnetic field where a current is induced on the sensor coil. The measured induced current may support identifying or determining a position of the instrument or object.

The electromagnetic field may be generated with a plurality of coils, such as three orthogonally placed coils. In some cases, the electromagnetic field may be generated using multiple coils or multiple sets of orthogonally placed coils (e.g., multiple sets of three orthogonally placed coils). Some electromagnetic navigation systems may include a plurality of coils that are used to generate an electromagnetic field that is sensed by a tracking device (e.g., the sensor coil). Some navigation systems, such as a StealthStation® surgical navigation system, may use such an electromagnetic field to track and/or illustrate a tracked position of an instrument.

Some navigation systems support electromagnetically navigating spine segments with small trackers in association with spine procedures. In some cases, multiple metal tools, implants, and robots used in association with the spine procedures may distort electromagnetic fields, thereby inhibiting successful electromagnetic navigation.

In the case of metal objects, electromagnetic distortions may depend on the type, size, and shape of the metal. The distortions may also depend on the pose of the metal object with respect to the emission device that emits signals associated with inducing a current at the sensor coil. In some cases, the distortions may depend on the frequency of the emitted electromagnetic fields. In some other cases of metal objects, magnetic permeabilities of stainless steels depend upon frequencies of applied magnetic fields. Further, skin depths of induced currents in all metals may depend upon magnetic permeabilities and frequencies of applied magnetic fields.

According to example aspects of the present disclosure, a system is described herein that supports navigation at ultra low to high frequencies (e.g., 300 Hz to 30 MHz) in association with eliminating electromagnetic distortion impacts on trackers. The techniques described herein for navigating at the ultra low to high frequencies may reduce coerced distortions as magnetic permeability decreases with increasing frequency. In some example aspects, navigating at such frequencies may reduce induced distortions at low frequencies and as skin depth decreases with increasing frequency. The system may use multiples of the frequencies (e.g., multiple ultra low to high frequencies) to determine or identify remaining coerced and induced distortions. For example, the system may support mechanisms for correcting the impact (e.g., mitigating the impact) of such distortions on tracking devices.

According to other example aspects of the present disclosure, the system may support navigation with swept frequencies in association with effectively eliminating electromagnetic distortions. The system may sweep across frequencies, sense and minimizes distortions, and navigate at multiple target frequencies (e.g., optimal frequencies). In an example, swept frequencies change ferromagnetic metal distortions from strongly coerced to strongly induced. Based on the frequency sweep, the system may identify a frequency that balances these interactions and minimizes distortions. For example, navigating at the identified frequency may achieve optimal levels (e.g., below corresponding threshold values) of coerced distortion and induced distortion. In some aspects, the identified frequency (also referred to herein as an optimal frequency) may depend on metal properties, geometries, and poses with respect to electromagnetic transmitters. Navigation with multiple such identified frequencies may minimize distortion impacts on tracking devices (e.g., tracking sensors).

Example aspects of the present disclosure may be implemented in association with navigation and segmental tracking supportive of surgical procedures (e.g., spine procedures) and other procedures in which the presence of metal objects is relatively high. For example, implementations of the present disclosure with respect to navigation at ultra low to high frequencies and/or navigation with swept frequencies may provide technical solutions that enable reliable segmental tracking in surgical procedures (e.g., spinal procedures) with multiple metal tools, implants, and robots. Aspects of the present disclosure support removing or accounting for the effects due to an interference or distortion caused by objects such as metal objects.

FIG. 1A illustrates an example of a system 100 that supports aspects of the present disclosure.

The system 100 includes a computing device 102, one or more imaging devices 112, a robot 114, a navigation system 118, a database 130, and/or a cloud network 134 (or other network). Systems according to other implementations of the present disclosure may include more or fewer components than the system 100. For example, the system 100 may omit and/or include additional instances of one or more components of the computing device 102, the imaging device(s) 112, the robot 114, navigation system 118, the database 130, and/or the cloud network 134. In an example, the system 100 may omit any instance of the computing device 102, the imaging device(s) 112, the robot 114, navigation system 118, the database 130, and/or the cloud network 134. The system 100 may support the implementation of one or more other aspects of one or more of the methods disclosed herein.

The computing device 102 includes a processor 104, a memory 106, a communication interface 108, and a user interface 110. Computing devices according to other implementations of the present disclosure may include more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging devices 112, the robot 114, the navigation system 118, the database 130, and/or the cloud network 134.

The memory 106 may be or include RAM, DRAM, SDRAM, other solid-state memory, any memory described herein, or any other tangible, non-transitory memory for storing computer-readable data and/or instructions. The memory 106 may store information or data associated with completing, for example, any step of the methods 400 described herein, or of any other methods. The memory 106 may store, for example, instructions and/or machine learning models that support one or more functions of the computing device 102, the imaging devices 112, the robot 114, and the navigation system 118. For instance, the memory 106 may store content (e.g., instructions and/or machine learning models) that, when executed by the processor 104, enable image processing 120, segmentation 122, transformation 124, registration 128, and/or navigation processing 129. Such content, if provided as in instruction, may, in some implementations, be organized into one or more applications, modules, packages, layers, or engines.

Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging devices 112, the robot 114, the navigation system 118, the database 130, and/or the cloud network 134.

The computing device 102 may also include a communication interface 108. The communication interface 108 may support receiving data or other information from an external source (e.g., the imaging devices 112, the robot 114, the navigation system 118, the database 130, the cloud network 134, and/or any other system or component separate from the system 100), and/or for transmitting instructions, data (e.g., navigation data, navigation frequencies, tracking information, distortion measurements, image data, etc.), or other information to an external system or device (e.g., another computing device 102, the imaging devices 112, the robot 114, the navigation system 118, the database 130, the cloud network 134, and/or any other system or component not part of the system 100). The communication interface 108 may include one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some implementations, the communication interface 108 may support communication between the device 102 and one or more other processors 104 or computing devices 102, whether to reduce the time needed to accomplish a computing-intensive task or for any other reason.

The computing device 102 may also include one or more user interfaces 110. The user interface 110 may be or include a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some implementations, the user interface 110 may support user modification (e.g., by a surgeon, medical personnel, a patient, etc.) of instructions to be executed by the processor 104 according to one or more implementations of the present disclosure, and/or to user modification or adjustment of a setting of other information displayed on the user interface 110 or corresponding thereto.

In some implementations, the computing device 102 may utilize a user interface 110 that is housed separately from one or more remaining components of the computing device 102. In some implementations, the user interface 110 may be located proximate one or more other components of the computing device 102, while in other implementations, the user interface 110 may be located remotely from one or more other components of the computer device 102.

The imaging device 112 may be operable to image anatomical feature(s) (e.g., a bone, veins, tissue, spine, etc.) and/or other aspects of patient anatomy to yield image data (e.g., image data depicting or corresponding to a bone, veins, tissue, spine, etc.). "Image data" as used herein refers to the data generated or captured by an imaging device 112, including in a machine-readable form, a graphical/visual form, and in any other form. In various examples, the image data may include data corresponding to an anatomical feature of a patient, or to a portion thereof. The image data may be or include a preoperative image, an intraoperative image, a postoperative image, or an image taken independently of any surgical procedure. In some implementations, a first imaging device 112 may support obtain first image data (e.g., a first image) at a first time, and a second imaging device 112 may support obtain second image data (e.g., a second image) at a second time after the first time. The imaging device 112 may be capable of taking a 2D image or a 3D image to yield the image data. The imaging device 112 may be or include, for example, an ultrasound scanner (which may include, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may include, for example, a transmitter, a receiver, a processor, and one or more antennae), or any other imaging device 112 suitable for obtaining images of an anatomical feature of a patient. The imaging device 112 may be contained entirely within a single housing, or may include a transmitter/emitter and a receiver/detector that are in separate housings or are otherwise physically separated.

In some implementations, the imaging device 112 may include more than one imaging device 112. For example, a first imaging device may provide first image data and/or a first image, and a second imaging device may provide second image data and/or a second image. In still other implementations, the same imaging device may support provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or include, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some implementations, the robot 114 may be configured to hold and/or manipulate an anatomical element during or in connection with a surgical procedure. The robot 114 may include one or more robotic arms 116. In some implementations, the robotic arm 116 may include a first robotic arm and a second robotic arm, though the robot 114 may include more than two robotic arms. In some implementations, one or more of the robotic arms 116 may support hold and/or maneuver the imaging device 112. In implementations where the imaging device 112 includes two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may include one or more sensors that enable the processor 104 (or a processor of the robot 114) to determine a precise pose in space of the robotic arm (as well as any object or element held by or secured to the robotic arm).

In some implementations, reference markers (e.g., navigation markers) may be placed on the robot 114 (including, e.g., on the robotic arm 116), the imaging device 112, or any other object (e.g., a surgical tool, operating equipment, etc.) in the surgical space. The reference markers may be tracked by the navigation system 118, and the results of the tracking may be used by the robot 114 and/or by an operator of the system 100 or any component thereof. In some implementations, the navigation system 118 can support track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some implementations, the navigation system 118 may include one or more electromagnetic sensors. In various implementations, the navigation system 118 may support track a position and orientation (e.g., a pose) of the imaging device 112, the robot 114, the robotic arm 116, and/or one or more surgical tools (or, more particularly, to track a pose of a navigated tracker attached, directly or indirectly, in fixed relation to the one or more of the foregoing). In some cases, the navigation system 118 may track the positions and orientations using one or more tracking devices 140 associated with (e.g., mechanically and/or electronically coupled to) to the imaging device 112, the robot 114, the robotic arm 116, and/or the one or more surgical tools.

The navigation system 118 may include a display for displaying one or more images from an external source (e.g., the computing device 102, imaging device 112, or other source) or for displaying an image and/or video stream from the one or more cameras or other sensors of the navigation system 118. In some implementations, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

In some aspects, the navigation system 118 may provide navigation information based on an electromagnetic field 151 (later illustrated at FIG. 1B) generated by a transmission device 136. For example, the transmission device 136 may be capable of generating an electromagnetic field 151 at multiple frequencies. In some aspects, the transmission device 136 may include an array of transmission coils 137 (also referred to herein as a transmission coil array (TCA)) capable of generating or forming the electromagnetic field 151 in response to respective currents driven through the transmission coils 137. In some aspects, the transmission device 136 may be referred to as an electromagnetic localizer.

The navigation system 118 may include tracking devices 140 capable of sensing the electromagnetic field 151 at the multiple frequencies. In some aspects, the tracking devices 140 may each have one or more sensing devices (e.g., a sensor coil) capable of sensing the electromagnetic field 151. Aspects of the navigation system 118 described herein may be implemented by navigation processing 129. Example aspects of the navigation system 118 are later described herein.

The processor 104 may utilize data stored in memory 106 as a neural network. The neural network may include a machine learning architecture. In some aspects, the neural network may be or include one or more classifiers. In some other aspects, the neural network may be or include any machine learning network such as, for example, a deep learning network, a convolutional neural network, a reconstructive neural network, a generative adversarial neural network, or any other neural network capable of accomplishing functions of the computing device 102 described herein. Some elements stored in memory 106 may be described as or referred to as instructions or instruction sets, and some functions of the computing device 102 may be implemented using machine learning techniques.

For example, the processor 104 may support machine learning model(s) 148 which may be trained and/or updated based on data (e.g., training data 146) provided or accessed by any of the computing device 102, the imaging device 112, the robot 114, the navigation system 118, the database 130, and/or the cloud network 134. The machine learning model(s) 148 may be built and updated based on the training data 146 (also referred to herein as training data and feedback).

For example, the machine learning model(s) 148 may be trained with one or more training sets included in the training data 146. In some aspects, the training data 146 may include multiple training sets. In some examples, based on the data (e.g., distortion magnitudes associated with signal frequencies, etc.), the neural network may generate one or more algorithms supportive of any of the techniques described herein.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information.

The database 130 may be configured to provide any such information to the computing device 102 or to any other device of the system 100 or external to the system 100, whether directly or via the cloud network 134. In some implementations, the database 130 may include candidate frequencies associated with the navigation system 118, distortion magnitudes associated with the frequencies and objects in an environment, one or more models 148 for compensating for the distortion in association with one or more of the frequencies, and the like. In some implementations, the database 130 may be or include part of a hospital image storage system, such as a picture archiving and communication system (PACS), a health information system (HIS), and/or another system for collecting, storing, managing, and/or transmitting electronic medical records including image data.

In some aspects, the computing device 102 may communicate with a server(s) and/or a database (e.g., database 130) directly or indirectly over a communications network (e.g., the cloud network 134). The communications network may include any type of known communication medium or collection of communication media and may use any type of protocols to transport data between endpoints. The communications network may include wired communications technologies, wireless communications technologies, or any combination thereof.

Wired communications technologies may include, for example, Ethernet-based wired local area network (LAN) connections using physical transmission mediums (e.g., coaxial cable, copper cable/wire, fiber-optic cable, etc.). Wireless communications technologies may include, for example, cellular or cellular data connections and protocols (e.g., digital cellular, personal communications service (PCS), cellular digital packet data (CDPD), general packet radio service (GPRS), enhanced data rates for global system for mobile communications (GSM) evolution (EDGE), code division multiple access (CDMA), single-carrier radio transmission technology (1×RTT), evolution-data optimized (EVDO), high speed packet access (HSPA), universal mobile telecommunications service (UMTS), 3G, long term evolution (LTE), 4G, and/or 5G, etc.), Bluetooth®, Bluetooth® low energy, Wi-Fi, radio, satellite, infrared connections, and/or ZigBee® communication protocols.

The Internet is an example of the communications network that constitutes an Internet Protocol (IP) network consisting of multiple computers, computing networks, and other communication devices located in multiple locations, and components in the communications network (e.g., computers, computing networks, communication devices) may be connected through one or more telephone systems and other means. Other examples of the communications network may include, without limitation, a standard Plain Old Telephone System (POTS), an Integrated Services Digital Network (ISDN), the Public Switched Telephone Network (PSTN), a Local Area Network (LAN), a Wide Area Network (WAN), a wireless LAN (WLAN), a Session Initiation Protocol (SIP) network, a Voice over Internet Protocol (VoIP) network, a cellular network, and any other type of packet-switched or circuit-switched network known in the art. In some cases, the communications network 120 may include of any combination of networks or network types. In some aspects, the communications network may include any combination of communication mediums such as coaxial cable, copper cable/wire, fiber-optic cable, or antennas for communicating data (e.g., transmitting/receiving data).

The computing device 102 may be connected to the cloud network 134 via the communication interface 108, using a wired connection, a wireless connection, or both. In some implementations, the computing device 102 may communicate with the database 130 and/or an external device (e.g., a computing device) via the cloud network 134.

The system 100 or similar systems may be used, for example, to carry out one or more aspects of any of the methods 200, 300, and/or 400 described herein. The system 100 or similar systems may also support other purposes.

Figure 1B:
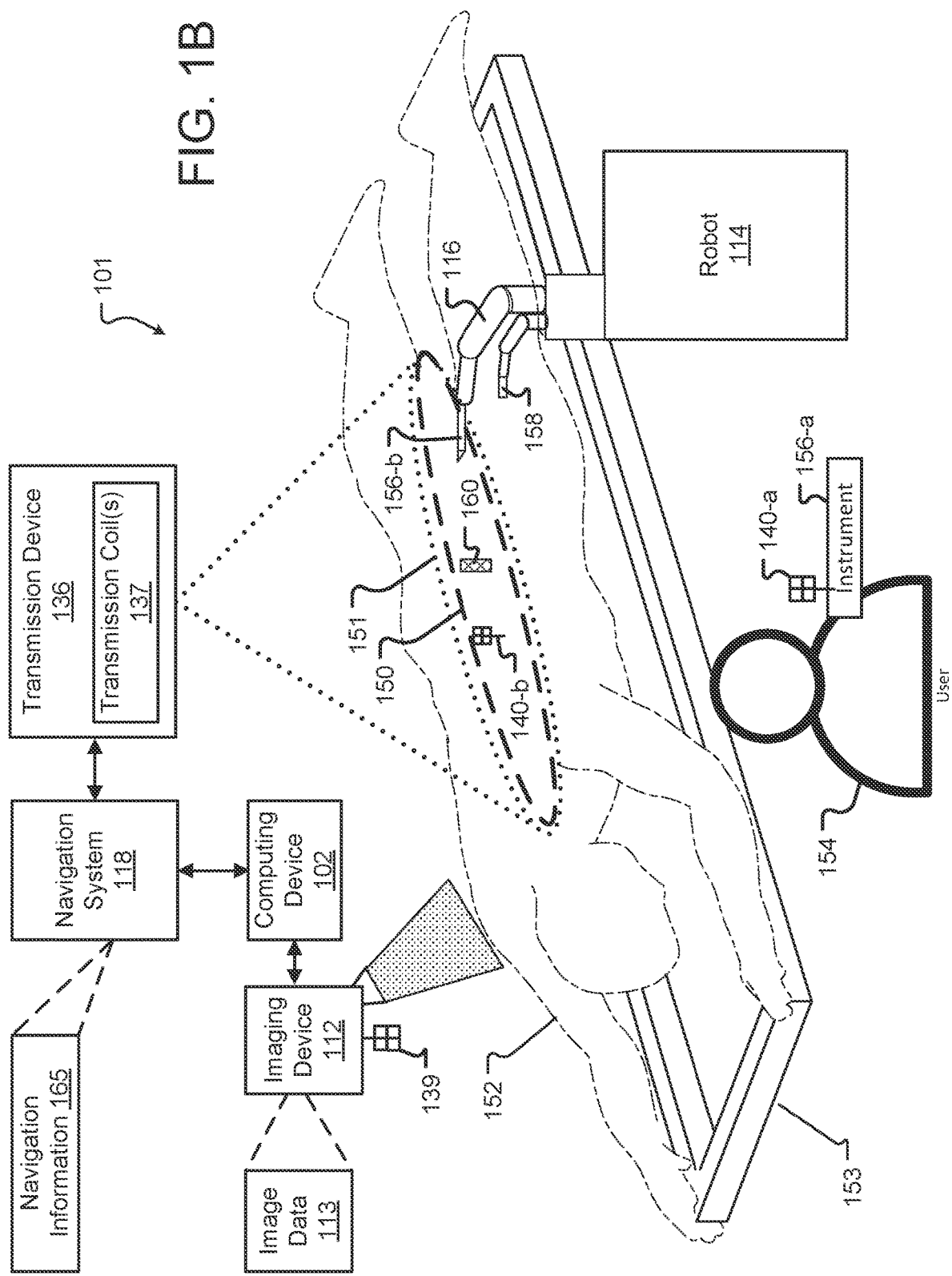

FIG. 1B illustrates an example implementation 101 of the system 100 that supports aspects of the present disclosure.

Referring to the example implementation 101 in FIG. 1B, the system 100 may support various purposes or procedures by one or more users, such as a user 154 (e.g., a surgeon, a medical technician, etc.). The system 100 may support determining or tracking a position of an instrument 156 (e.g., instrument 156-*a*, instrument 156-*b*, etc.) or multiple instruments 156 in a volume. The position may include both a three-dimensional XYZ location and orientation. Orientation may include one or more degree of freedom, such as three degrees of freedom. The position and orientation may be referred to as pose information. The example aspects of the system 100 may be implemented, for example, by navigation system 118.

Tracking the position of the instrument 156 may assist the user 154 in determining a position of the instrument 156, even if the instrument 156 is not directly viewable by the user 154 or a visual imaging device (e.g., imaging device 112, a camera) of the system 100. Various procedures may block the visibility of instrument 156. An example includes a surgical procedure, such as performing low invasive, including a minimally invasive procedures including a spinal procedure, neurological procedure, positioning a deep brain simulation probe, or other surgical procedures on a living subject. Other examples of procedures include performing a repair or assembling an inanimate system, such as a robotic system, assembling portions of an airframe or an automobile, or the like.

In various embodiments, for example, the subject 152 may be a living subject (e.g., a human subject) and the procedure may be performed on the subject 152. It is understood, however, that the system 100 supports tracking and/or navigating the instrument 156 relative to any subject 152 for any appropriate procedure. Tracking or navigating an instrument for a procedure, such as a surgical procedure, on a human or living subject is an example.

The system 100 may include a support 153 (e.g., a table, a platform, etc.) capable of supporting or holding the subject 152 during a procedure (e.g., medical imaging, a surgical procedure, etc.). The same or different supports 153 may support different portions of a procedure.

The system 100 may acquire image data 113 via the imaging device 112 at any temporal instance. For example, the system 100 may acquire the image data 113 during a surgical procedure or prior to a surgical procedure. The system 100 may display static and/or real-time images on a display device (e.g., user interface 110 of computing device 102) based on the image data 113.

The system 100 may support tracking the instrument 156 in a trackable volume 150 using an electromagnetic field 151 produced by the transmission device 136. For example, the transmission device 136 may include a transmitter antenna or transmitting coil array (e.g., including transmission coils 137) capable of producing the electromagnetic field 151. The system 100 may track the pose (e.g., position, coordinates, orientation, etc.) of the instrument 156 in the tracking volume 150 relative to the subject 152. In some aspects, the system 100 may display, via a user interface of the computing device 102, icons corresponding to any tracked instruments 156. For example, the system 100 may superimpose such icons on and/or adjacent an image displayed on the user interface. The terms "tracking volume," "trackable volume," "navigation volume," and "volume" may be used interchangeably herein.

In some aspects, the transmission device 136 may be referred to as a localizer. For example, the transmission device 136 may be an electromagnetic localizer that is operable to generate electromagnetic fields (e.g., the electromagnetic field 151) via an array of transmission coils 137 (also referred to herein as a transmitting coil array (TCA)). The TCA may include one or more coil groupings or arrays. In various embodiments, more than one group is included and each of the groupings may include three coils, also referred to as trios or triplets.

The transmission device 136 may drive current through the coils of the coil groupings, thereby powering the coils to generate or form an electromagnetic field 151. As the current is driven through the coils, the electromagnetic field 151 (or electromagnetic fields 151) will extend away from the transmission coils 137 and form a navigation domain (e.g., volume 150). The volume 150 may include any portion (e.g., the spine, one or more vertebrae, the brain, an anatomical element, or a portion thereof, etc.) of the subject 152, for example, as configured via the system 100. The transmission coils 137 may be powered through a controller device and/or power supply provided by the system 100.

The system 100 may include a tracking device 139. The tracking device 139 may be a dynamic preference frame (DRF) or reference frame tracker. In an example, the tracking device 139 may be positioned such that the tracking device 139 is in a fixed pose relative to the subject 152. For example, the tracking device 139 may be coupled to the imaging device 112, and the imaging device 112 may be stationary (e.g., in a fixed pose).

The navigation system 118 may track the pose and/or movement of the tracking devices 140 relative to the tracking device 139. In an example, the tracking device 140-*a* may be coupled to the instrument 156-*a*, and the navigation system 118 may track the pose and/or movement of the instrument 156-*a* based on the pose and/or movement of the tracking device 140-*a*. Additionally, or alternatively, the tracking device 140-*b* may be coupled to the instrument 156-*b*, and the navigation system 118 may track the pose and/or movement of the instrument 156-*b* based on the pose and/or movement of the tracking device 140-*b*.

Accordingly, for example, the navigation system 118 may support determining the position of the instrument 156-*a* and/or instrument 156-*b* relative to the DRF. The instruments 156 may be, for example, tools such as a surgical tool, a drill, a lead, or the like and may be tracked by the navigation system 118 in the volume 150. The instruments 156 may be freely moveable, such as by the user 154 or the robot 114, relative to the tracking device 139.

The tracking devices 140 may include or be provided as sensors (also referred to herein as tracking sensors). The sensors may sense a selected portion or component of the electromagnetic field(s) generated by the transmission coils 137 of the transmission device 136. In various embodiments, the transmission coils 137 may be formed of wire or thread of conductive material. The transmission coils 137 may also be referred to as tracking or sensing coils capable of sensing and measuring a magnetic field strength, a component of a field, and the like.

The navigation system 118 may support registration (e.g., through registration 128) of the volume 150 to an image space of the subject 152. The navigation system 118 may support superimposing an icon representing an instrument 156 (e.g., instrument 156-*a*, instrument 156-*b*, etc.) on the image. The system 100 may support the delivery of tracking information from the tracking devices 140 to the navigation system 118. The tracking information may include, for example, data associated with the magnetic fields sensed by the tracking devices 140.

The tracking devices 140 may communicate sensor information to the navigation system 118 for determining a position of the tracked portions relative to each other and/or for localizing the instrument 156-*a* relative to the image. The imaging system 24 may support acquiring image data 113 to generate or produce the image of the subject 152. It is understood, however, that other appropriate imaging systems may also be used. The navigation system 118 and/or transmission device 136 may include a controller that supports operating and powering the transmission coils 137.

The transmission device 136 (and array formed by transmission coils 137) may be operated to transmit at any power and/or may be powered with any current associated with generating an electromagnetic field 151 described herein. For example, transmission device 136 (and transmission coils 137) may be operated to transmit in a power range of about 0.01 milli-watts (mW) to about 30 watts (W), including about 0.1 mW to about 10 W, and further including about 0.1 mW to about 5 W, but is not limited thereto. In some example implementations, the transmission device 136 (and transmission coils 137) may be operated to transmit in a power range in which the lowest transmission power is 1 µW.

In some cases, objects not being tracked by the navigation system 118 may be present in or near the electromagnetic field 151 (or electromagnetic fields 151) generated by the transmission coils 137. The objects may be positioned within the volume 150 and/or interfere or be affected by the electromagnetic field 151. As discussed herein, the various objects or elements may be referred to as interfering or disruptive members, objects, or elements. In some aspects, each of the interfering members may have a current induced therein that generates a field separate from the electromagnetic field 151 (or electromagnetic fields 151) generated by the transmission coils 137.

The objects may include ferromagnetic objects and/or non-ferromagnetic objects. In some cases, the ferromagnetic objects may be conductive objects and/or the non-ferromagnetic objects may be conductive objects. Examples of such objects may include metal tools (e.g., tools different from instruments 156, tools not tracked by navigation system 118, etc.), medical implants (e.g., implant 160 later described herein), other robots 114, end effectors 158 associated with the robots 114, and the like.

In an example case of a ferromagnetic object, characteristics of the ferromagnetic object may impact the ability in which the navigation system 118 is able to track the tracking devices 140. For example, the ferromagnetic object may introduce a distortion to the electromagnetic field 151. The magnetic permeability of the ferromagnetic object (and correspondingly, the magnitude of the distortion) may depend on the frequency of the applied electromagnetic field 151, and the magnitude of the distortion may correspond to the resulting magnetic permeability. Accordingly, for example, the magnitude of the distortion produced by the ferromagnetic object may change, by superposition, the electromagnetic field 151.

In an example case of a non-ferromagnetic object such as a conductive object, eddy currents may be produced in the non-ferromagnetic object due to the electromagnetic field 151. The eddy currents may then generate electromagnetic fields that are in addition to the electromagnetic field 151. Accordingly, for example, the electromagnetic field produced by the non-ferromagnetic object may change, by superposition, the electromagnetic field 151.

In various embodiments, the conductive objects may include all or a portion of the computing device 102, the imaging device 112, the support 153, and/or other procedure instrumentation. It is understood, however, that various conductive members may be interfering members even if not specifically identified herein. Aspects of the present disclosure support implementations that address instances in which any quantity of objects (e.g., ferromagnetic objects, non-ferromagnetic objects, etc.) are present in or near the electromagnetic field 151.

Example implementations of the present disclosure supportive of compensating for such distortions caused by the non-ferromagnetic objects and/or ferromagnetic objects are described with reference to the following figures.

Figure 2A:
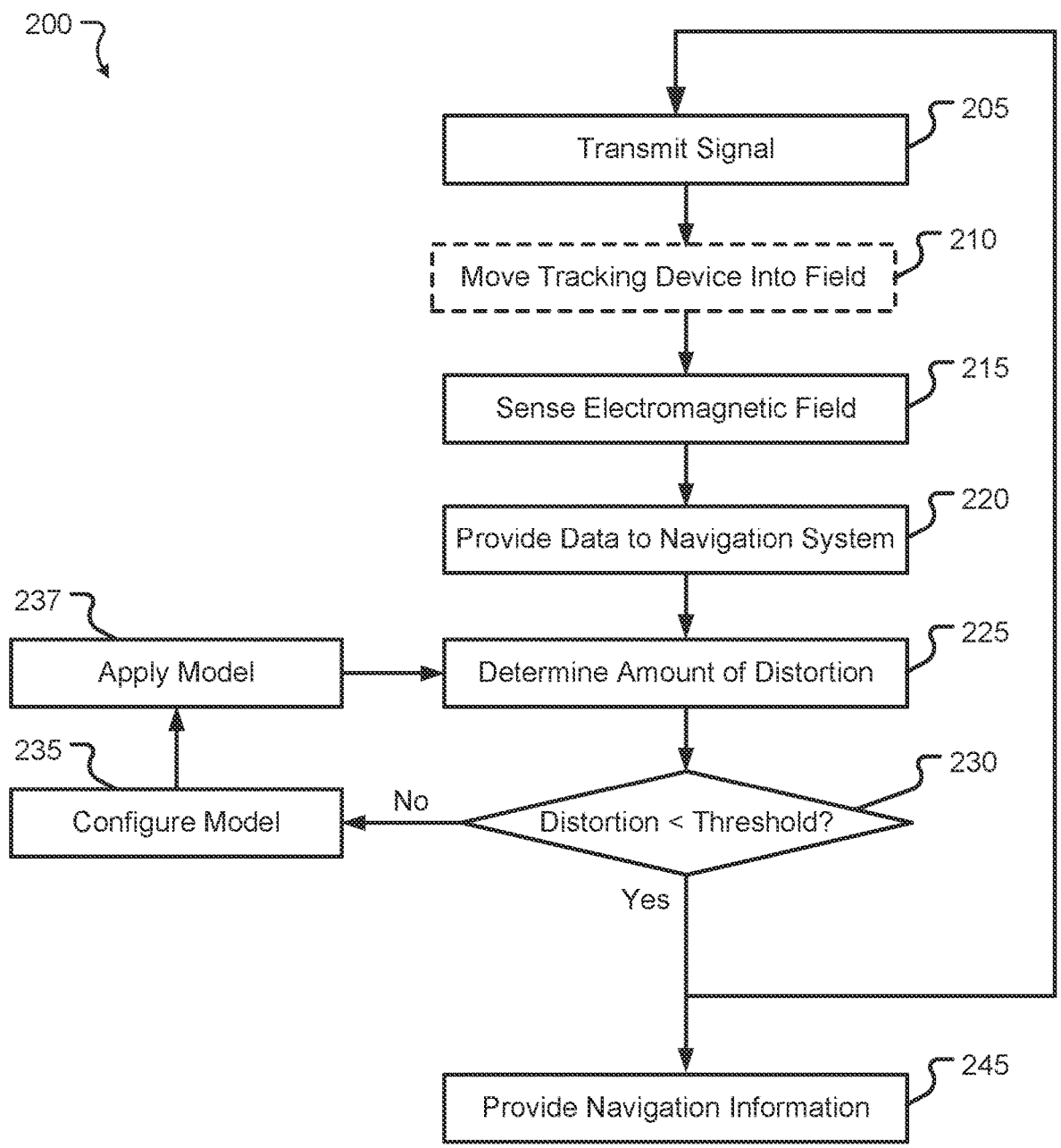
FIG. 2A illustrates an example of a process flow in accordance with aspects of the present disclosure.

FIG. 2A illustrates an example of a process flow 200 that supports navigation at ultra low to high frequencies in accordance with aspects of the present disclosure.

In some examples, process flow 200 may implement aspects of a system 100 described with reference to FIGS. 1A and 1B. The process flow 200 is described with reference to FIGS. 1A, 1B, and 2B. In the following description of the process flow 200, the operations may be performed in a different order than the order shown, or the operations may be performed in different orders or at different times. Certain operations may also be left out of the process flow 200, or other operations may be added to the process flow 200.

It is to be understood that a computing device 102, navigation system 118, and/or transmission device 136 may perform a number of the operations of process flow 200, and any device (e.g., another computing device 102, navigation system 118, transmission device 136, etc. of the system 100) may perform the operations shown.

At 205, the navigation system 118 may transmit a signal according to a frequency, a set of frequencies, and/or a set of frequency bands. In an example, the frequency, set of frequencies, and/or frequency bands may be included in a frequency range of about 300 Hz to 30 MHz. For example, the navigation system 118 may drive a single transmission coil 137, a set of transmission coils 137, or an array of transmission coils 137 according to a signal frequency, a set of frequencies, or a set of frequency bands, thereby generating electromagnetic field 151 associated with the signal frequency, the set of frequencies, or the set of frequency bands. In an example, generating the electromagnetic field 151 may define the volume 150.

At 210, a tracking device 140 may be moved into the electromagnetic field 151. For example, the tracking device 140 (or an instrument 156 to which the tracking device 140 is coupled) may be moved into the electromagnetic field 151 by the user 154 or the robot 114 (e.g., autonomously or in response to a command by the user 154). In some examples, the tracking device 140 may already be positioned within the volume 150, and moving the tracking device 140 at 210 may be omitted.

At 215, the tracking devices 140 may sense the electromagnetic field 151 and any distortions resulting from the electromagnetic field 151.

At 220, the tracking devices 140 may provide data to the navigation system 118 indicative of the sensing of the electromagnetic field 151 and any corresponding distortions. For example, at 220, the tracking device 140 may provide a signal indicating a measurement or sensed field in the volume 150. In an example, the signal may include data indicating the measurement or sensed field. In some examples, the signal may include pose information of the tracking device 140.

At 225, the navigation system 118 may determine an amount of distortion present in the electromagnetic field 151, such as within the volume 150, based on the data provided by the tracking device 140. In some aspects, at 225, the navigation system 118 may use various metrics to determine the amount of distortion. For example, the navigation system 118 may determine metrics from the received signals. In some aspects, the navigation system 118 may construct the metrics from pose information of the tracking device 140.

At 230, the navigation system 118 may determine whether the amount of distortion is less than a distortion threshold (e.g., Distortion Less Than Threshold?). In some alternative aspects (not illustrated), at 230, the navigation system 118 may determine whether any distortion is present (e.g., Distortion Present?).

If the navigation system 118 determines that the amount of distortion is less than the distortion threshold (e.g., Distortion Less Than Threshold?=Yes), the navigation system 118 may proceed to 245 and/or return to 205.

Additionally, or alternatively, if at 230 the navigation system 118 determines based on the data provided by the tracking device 140 that the amount of distortion is greater than or equal to the distortion threshold (e.g., Distortion Less Than Threshold?=No), the navigation system 118 may configure (at 235) a model to compensate for the distortion. In some aspects, the navigation system 118 may store the model (or models) to memory 106 and/or database 130. For example, the navigation system 118 may recall the model (or models) for future instances in which similar distortion levels and/or distortion characteristics are determined by the navigation system 118.

At 237, the navigation system 118 may apply the configured model to compensate for the distortion, thereby reducing the impact of the distortion on the electromagnetic field 151. For example, applying the configured model may reduce the distortion to a distortion level less than the distortion threshold. In some examples, applying the model may include effectively eliminating the distortion. In some aspects, the process flow 200 may include repeating 225 through 237, for example, until the distortion level is less than the distortion threshold.

At 245, the navigation system 118 may provide navigation information 165 associated with the volume 150 and the tracking device 140. For example, the tracking devices 140 may provide sensor information (e.g., indicative of pose information of the tracking devices 140) to the navigation system 118 based on applying the model. In an example, using the navigation information 165, the user 154 and/or robot 114 may navigate a surgical procedure.

In some aspects, the system 100 may support repeating any of 205 through 245 of the process flow 200 for any quantity of frequencies.

Figure 2B:
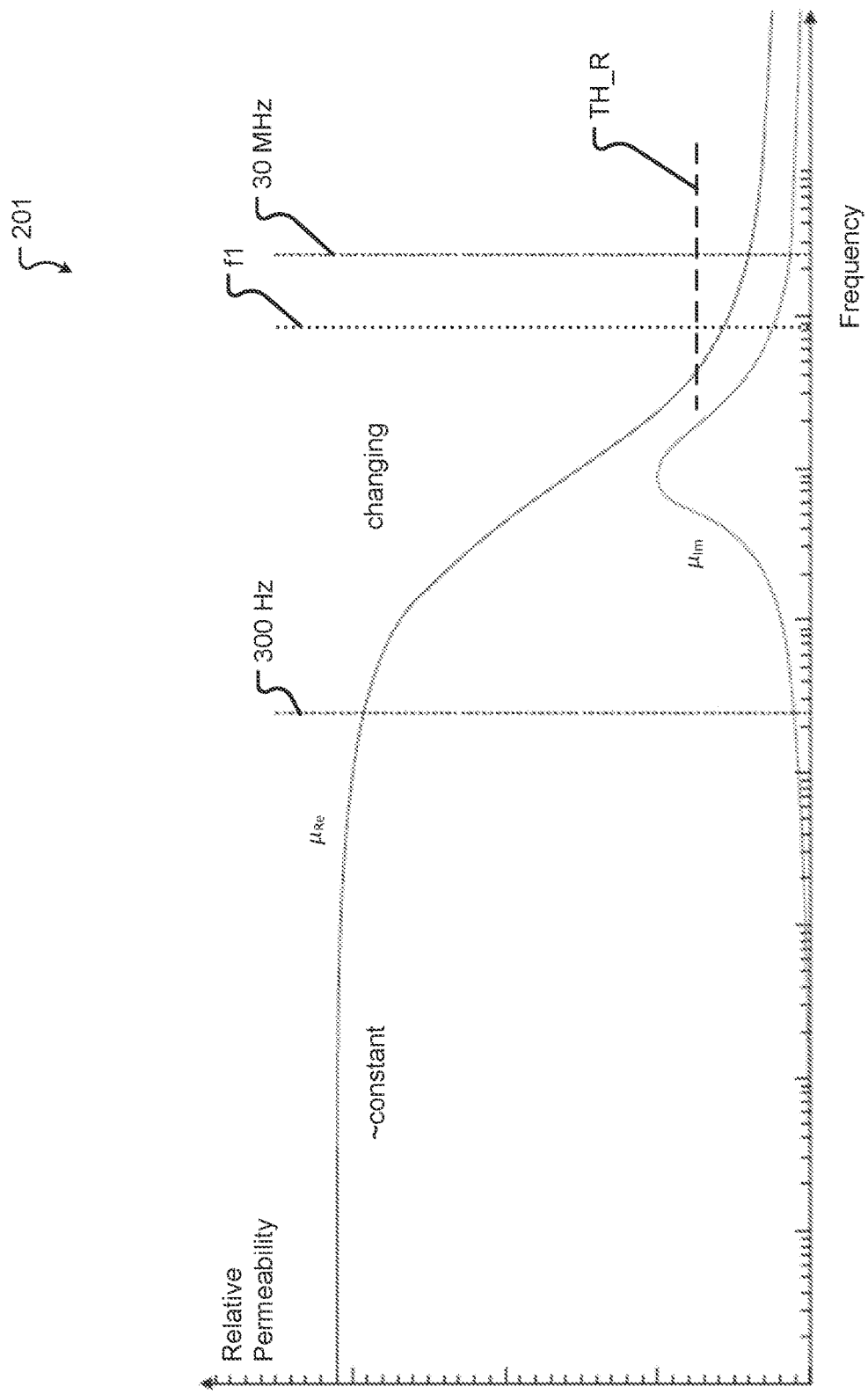
FIG. 2B illustrates an example response of a ferromagnetic object in accordance with aspects of the present disclosure.

FIG. 2B illustrates an example magnetic response 201 of a ferromagnetic object based on the frequency of the applied electromagnetic field 151. The example magnetic response 201 includes real ($\mu_{Re}$) and imaginary ($\mu_{Im}$) components. In some aspects, in the case of a ferromagnetic object, determining the amount of distortion at 225 of FIG. 2A may be based on a relative permeability (illustrated in the example magnetic response 201) of the ferromagnetic object.

The ferromagnetic object may be an instrument 156 described with reference to FIG. 1B, but is not limited thereto. In an example, the data provided to the navigation system 118 by the tracking device 140 (at 220) may be indicative of the electromagnetic field 151 as sensed by the tracking device 140 with respect to a frequency f1 and may be indicative of a magnetic distortion associated with the instrument 156 (or a portion of the instrument 156, for example, a magnetic portion of the instrument 156).

In determining the amount of distortion (at 225), the navigation system 118 may calculate a magnetic permeability $\mu_m$ associated with the instrument 156 at the frequency f1. For example, the magnetic permeability $\mu_m$ may be associated with the magnetic portion of the instrument 156. The magnetic permeability $\mu_m$ of the magnetic portion is the ability of the magnetic portion (e.g., the magnetic material) to support formation of magnetic fields. For example, the magnetic portion may introduce distortion to the electromagnetic field 151 due to the magnetic permeability $\mu_m$ of the magnetic portion that results in response to the electromagnetic field 151 at the frequency f1.

In some aspects, in determining the amount of distortion (at 225), the navigation system 118 may calculate a relative permeability $\mu_r$ associated with the instrument 156 at the frequency f1. For example, the relative permeability $\mu_r$ may be associated with the magnetic portion of the instrument 156. The relative permeability $\mu_r$ of the magnetic portion may be equal to the ratio of the magnetic permeability $\mu_m$ of the magnetic portion to the permeability of free space $\mu_0$, as illustrated in example equation (1) below.

$$\mu_r = \mu_m/\mu_0 \quad (1)$$

The navigation system 118 may continue to calculate the relative permeability $\mu_r$ while changing the frequency associated with generating the electromagnetic field 151.

In some aspects, to identify a frequency at which to generate the electromagnetic field 151 and thereby provide navigation, the navigation system 118 may start at a relatively high frequency (e.g., at or near 30 MHz) associated with generating the electromagnetic field 151 and determine the relative permeability $\mu_r$ of the object due to the electromagnetic field 151. If the relative permeability $\mu_r$ is below a threshold value TH_R, the navigation system 118 may decrease the frequency until the relative permeability $\mu_r$ exceeds the threshold value TH_R (e.g., via a frequency sweep later described with reference to FIGS. 3A through 3C), thereby identifying frequencies that may support effective navigation. In some other aspects, for a frequency at which the relative permeability $\mu_r$ exceeds the threshold value TH_R, the navigation system 118 may configure and apply a model as described herein to reduce the relative permeability $\mu_r$ to a level equal to or less than the threshold value TH_R. In some other example aspects, for a frequency at which the relative permeability $\mu_r$ does not exceed the threshold value TH_R, the navigation system 118 may configure and apply a model as described herein to further reduce the relative permeability $\mu_r$.

Accordingly, for example, the navigation system 118 may identify a frequency range associated with the electromagnetic field 151 within which distortion to the electromagnetic field 151 due to the relative permeability $\mu_r$ of the object is minimized. For example, the navigation system 118 may identify that the impact of the relative permeability $\mu_r$ of the object on the ability of the navigation system 118 to effectively track the tracking device 140 will be minimized.

Figure 3A:
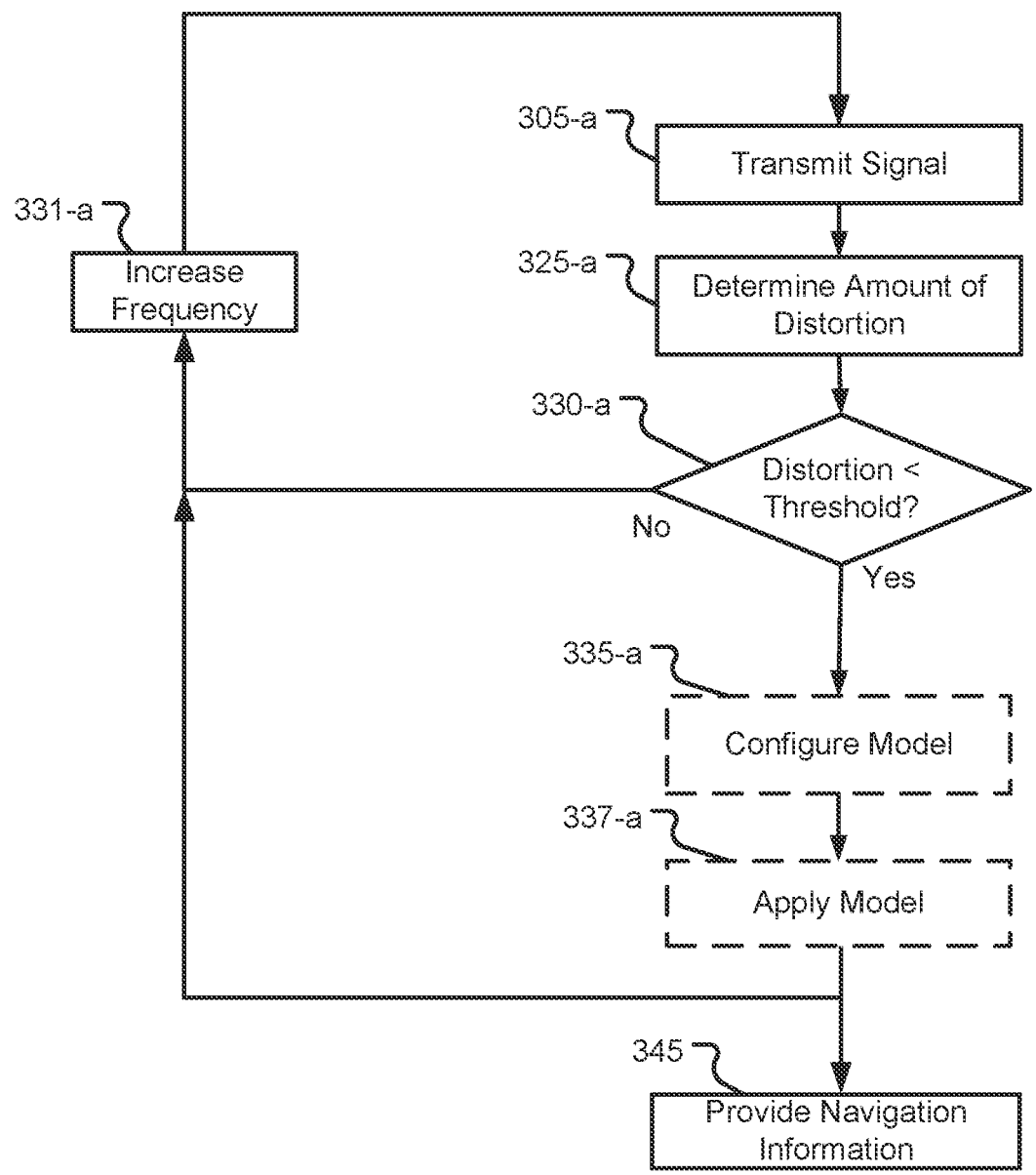
FIGS. 3A and 3B illustrate example process flows in accordance with aspects of the present disclosure.
Figure 3B:
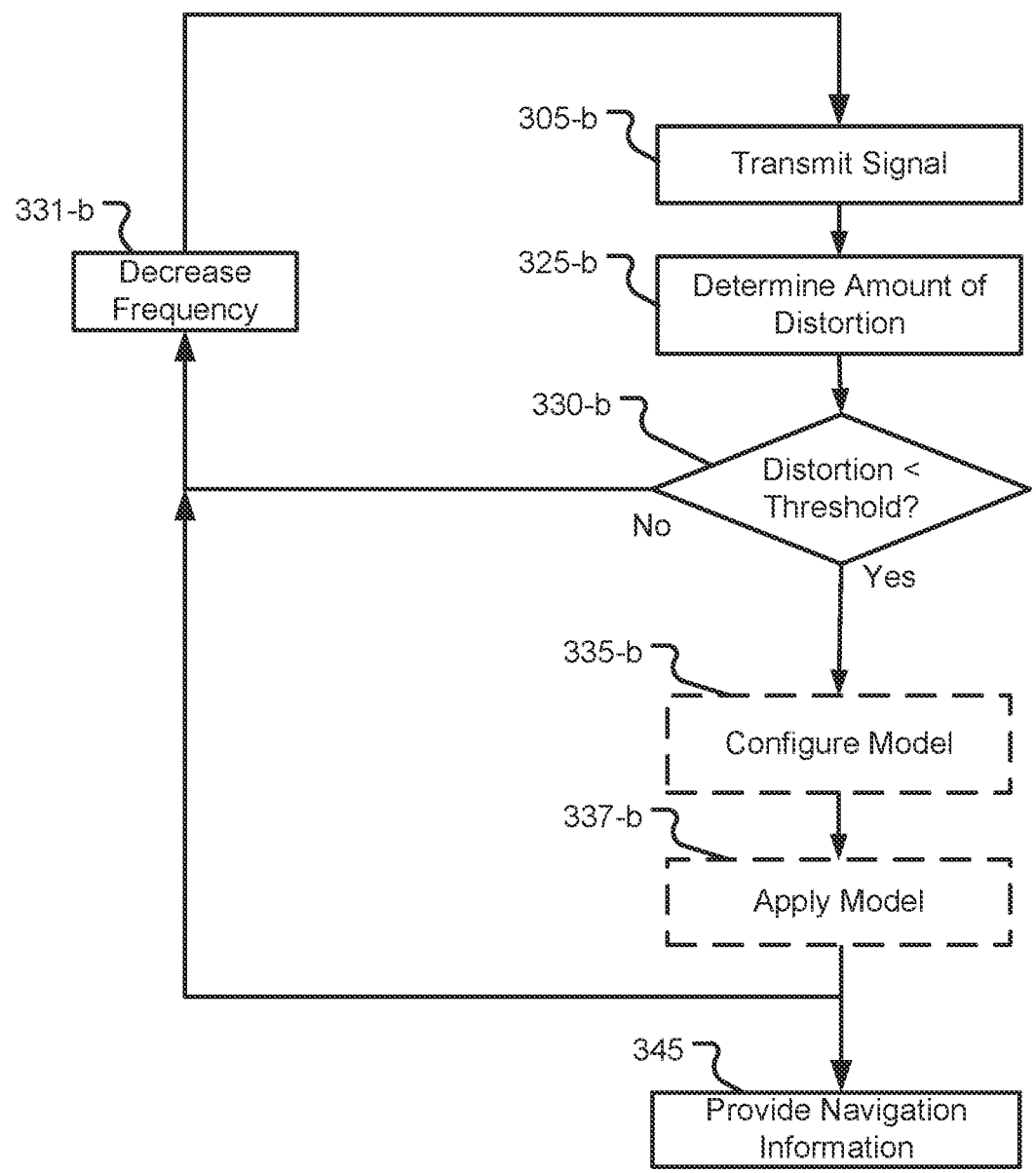
Figure 3C:
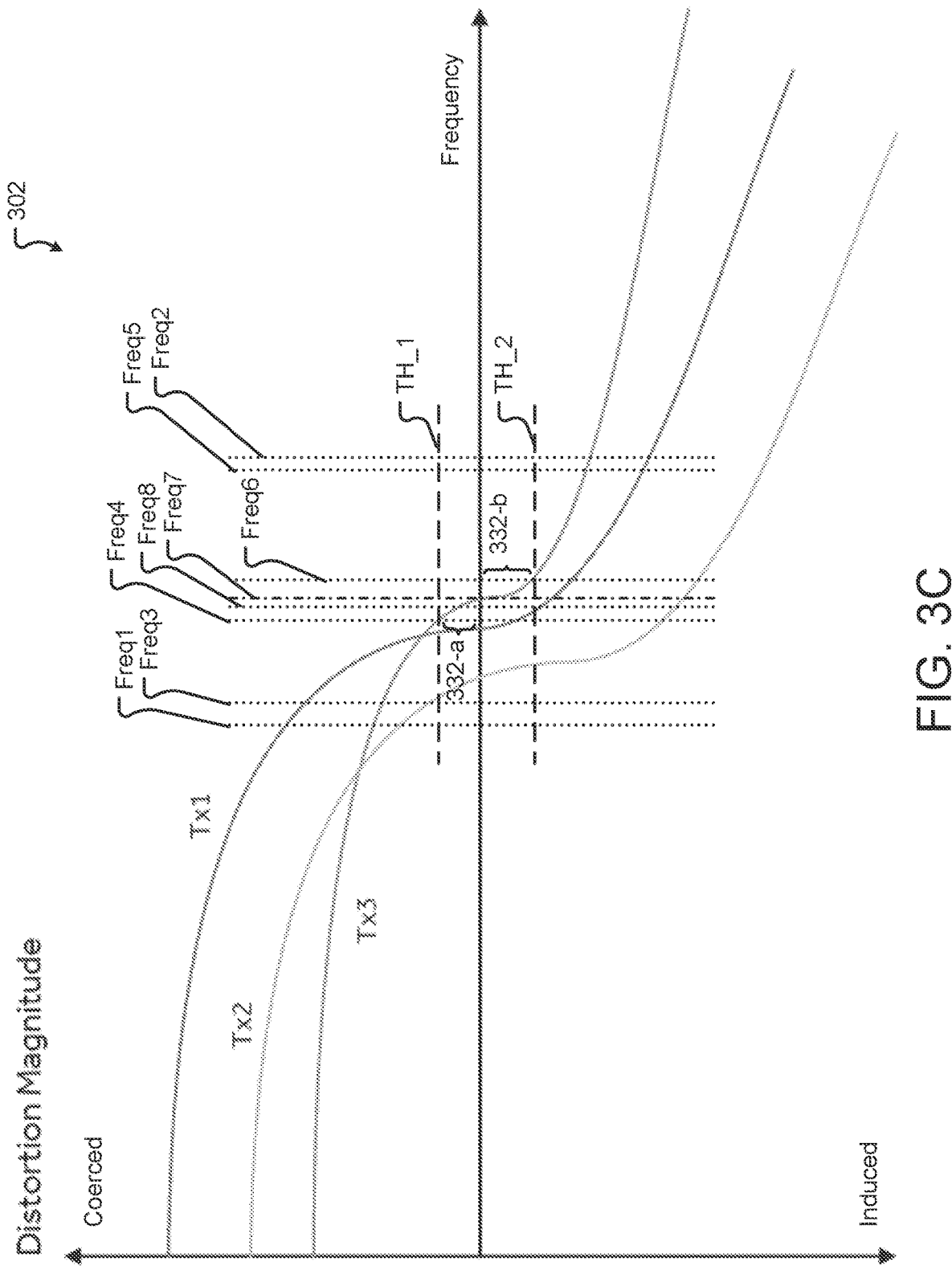
FIG. 3C illustrates an example of distortion magnitudes in accordance with aspects of the present disclosure.

FIG. 3A illustrates an example of a process flow 300 that supports navigation with swept frequencies in accordance with aspects of the present disclosure. FIG. 3B illustrates an example of a process flow 301 that supports navigation with swept frequencies in accordance with aspects of the present disclosure. FIG. 3C illustrates example distortion magnitudes with respect to frequency for respective transmission coils 137 (labeled as "Tx1" through "Tx3" in FIG. 3C) of the transmission device 136.

Aspects of FIGS. 3A and 3B support reducing the effect of distortions caused by the ferromagnetic objects and/or non-ferromagnetic objects based on the frequency of the applied electromagnetic field 151. Distortion such as a magnetic distortion associated with a ferromagnetic object may be referred to herein as a "coerced distortion." Distortion such as a conductive distortion associated with a conductive object (e.g., a ferromagnetic object or a non-ferromagnetic object) may be referred to herein as an "induced distortion." Aspects of described with reference to FIGS. 3A and 3B support navigation with swept frequencies in association with compensating for the distortions caused by ferromagnetic objects and/or non-ferromagnetic objects.

In some examples, process flows 300 and 301 may implement aspects of a system 100 described with reference to FIGS. 1A and 1B. The process flows 300 and 301 are described with reference to FIGS. 1A, 1B, and 3C. In the following description of the process flows 300 and 301, the operations may be performed in a different order than the order shown, or the operations may be performed in different orders or at different times. Certain operations may also be left out of the process flows 300 and 301, or other operations may be added to the process flows 300 and 301. The process flows 300 and 301 include aspects of the process flow 200, and descriptions of like elements are omitted for brevity.

It is to be understood that a computing device 102, navigation system 118, and/or transmission device 136 may perform a number of the operations of process flows 300 and 301, and any device (e.g., another computing device 102, navigation system 118, transmission device 136, etc. of the system 100) may perform the operations shown.

According to example aspects of the present disclosure, the navigation system 118 may transmit a signal according to a frequency in a frequency range of Freq1 (e.g., about 300 Hz) to Freq2 (e.g., about 30 MHz). For example, the navigation system 118 may drive an array of transmission coils 137 according to the frequency, thereby generating the electromagnetic field 151 in association with the frequency. Example aspects are described with reference to the navigation system 118 and the distortion magnitude (illustrated at FIG. 3C) associated with a transmission coil 137 referenced as "Tx1".

In an example later described with reference to FIG. 3A, the navigation system 118 may drive the array of transmission coils 137 starting at or near Freq1. In another example, the navigation system 118 may initially drive the array starting at any relatively low frequency within the frequency range. For example, the navigation system 118 may initially drive the array starting at a frequency higher than Freq1.

In an example, later described with reference to FIG. 3B, the navigation system 118 may initially drive the array starting at any relatively high frequency within the frequency range. For example, the navigation system 118 may drive the array of transmission coils 137 starting at or near Freq2. In some examples, the navigation system 118 may initially drive the array starting at a frequency lower than Freq2.

For the initial frequency, the navigation system 118 may determine an amount of distortion present in the electromagnetic field 151, such as within the volume 150, based on data provided by the tracking device 140. In some aspects, the navigation system 118 may determine whether the amount of induced distortion is less than a distortion threshold. Example aspects of driving the transmission coils 137 starting at a relatively low frequency and a relatively high frequency are respectively described with reference to FIGS. 3A and 3B.

Referring to the process flow 300 of FIG. 3A, an example of driving the array of transmission coils 137 starting at Freq1 is described herein.

At 305-*a*, the navigation system 118 may transmit a signal according to Freq1 (e.g., about 300 Hz).

At 325-*a*, the navigation system 118 may determine the amount of distortion at Freq1. In some aspects, the navigation system 118 may determine the amount of distortion using like aspects described with reference to 225 of FIG. 2A. In some aspects later described herein, the navigation system 118 may determine whether the distortion is primarily coerced or primarily induced, for example, by further transmitting signals at other frequencies and determining resulting distortions.

At 330-*a*, the navigation system 118 may determine whether the amount of distortion at Freq1 is less than a distortion threshold TH_1 (e.g., Distortion Less Than Threshold?). In an example, the navigation system 118 may determine that the amount of distortion is not less than the distortion threshold (e.g., Distortion Less Than Threshold?=No).

The navigation system 118 may iteratively optimize (e.g., adjust, increase, etc.) the frequency associated with the electromagnetic field 151 until the distortion is less than the distortion threshold. For example, at 331-*a*, the navigation system 118 may increase the frequency associated with the electromagnetic field 151. In an example, the navigation system 118 may transmit (at 305-*a*) the signal according to a frequency Freq3 that is higher than Freq1.

The navigation system 118 may return to 325-*a* and determine whether the amount of distortion according to Freq3 is less than the distortion threshold TH_1 (e.g., Distortion Less Than Threshold?).

The navigation system 118 may continue increasing the frequency associated with the electromagnetic field 151 until reaching a frequency Freq4 at which the amount of distortion is less than the distortion threshold TH_1 (e.g., Distortion Less Than Threshold?=Yes).

For example, if the navigation system 118 determines at 330-*a* that the magnitude 332-*a* of distortion (e.g., at Freq4) is less than the distortion threshold TH_1 (e.g., Distortion Less Than Threshold?=Yes), the navigation system 118 may proceed to 345. Additionally, or alternatively, the navigation system 118 may proceed to 335-*a*, aspects of which are later described herein.

At 345, the navigation system 118 may provide navigation information 165 associated with the volume 150 and the tracking device 140 for Freq4 in which the distortion is below the distortion threshold TH_1 (e.g., the magnitude 332-*a* of distortion is less than the magnitude associated with the distortion threshold TH_1).

In some examples, the navigation system 118 may continue to increase the frequency up to a frequency Freq7 at which the magnitude 332-*a* of distortion is equal to zero, and the navigation system 118 may provide navigation information 165 for the frequency range of Freq4 through Freq7.

Example aspects of the process flow 300 further include applying a model to further reduce the distortion. For example, if the navigation system 118 determines at 330-*a* that the distortion is below the distortion threshold TH_1 (e.g., Distortion Less Than Threshold?=Yes), the navigation system 118 may configure a model (or models) to compensate for the remaining distortion.

For example, at 335-*a*, the navigation system 118 may configure the model (or models). At 337-*a*, the navigation system 118 may apply the model to compensate for the remaining distortion. In some aspects, the navigation system 118 may store the model (or models) to memory 106 and/or database 130. For example, the navigation system 118 may recall the model for future instances in which similar levels of distortion are determined by the navigation system 118. Accordingly, for example, the navigation system 118 may develop and apply a model that compensates for remaining distortions within the frequency range from Freq4 to Freq7.

In an example, the model may include a first-principles model of received signals as a function of frequency in the presence of coerced distortion, extrapolated to a frequency with favorable features (e.g., known or otherwise easily treated material properties). In another example, the model may be based on machine learning, taking distorted signals at different frequencies as input and providing as output an estimation of what the undistorted signal at a target frequency (e.g., a useful frequency) would have been. In some aspects, the navigation system 118 may apply the model to correct for or remove distortion that is sensed in the electromagnetic field 151 and incorporated in the signal provided by a tracking device 140.

Referring to the process flow 301 of FIG. 3B, an example of driving the array of transmission coils 137 starting at Freq2 is described herein.

At 305-*b*, the navigation system 118 may transmit a signal according to Freq2 (e.g., about 30 MHz).

At 325-*b*, the navigation system 118 may determine the amount of distortion at Freq2. In some aspects, the navigation system 118 may determine the amount of distortion using like aspects described with reference to 225 of FIG. 2A. In some aspects later described herein, the navigation system 118 may determine whether the distortion is primarily coerced or primarily induced, for example, by further transmitting signals at other frequencies and determining resulting distortions.

At 330-*b*, the navigation system 118 may determine whether the amount of distortion at Freq2 is less than an distortion threshold TH_2 (e.g., Distortion Less Than Threshold?). In an example, the navigation system 118 may determine that the amount of distortion is not less than the distortion threshold (e.g., Distortion Less Than Threshold?=No).

The navigation system 118 may iteratively optimize (e.g., adjust, decrease, etc.) the frequency associated with the electromagnetic field 151 until the distortion is less than the distortion threshold. For example, at 331-*b*, the navigation system 118 may decrease the frequency associated with the electromagnetic field 151. In an example, the navigation system 118 may transmit (at 305-*b*) the signal according to a frequency Freq5 that is lower than Freq2.

The navigation system 118 may return to 325-*b* and determine whether the amount of distortion according to Freq5 is less than the distortion threshold TH_2 (e.g., Distortion Less Than Threshold?).

The navigation system 118 may continue decreasing the frequency associated with the electromagnetic field 151 until reaching a frequency Freq6 at which the amount of distortion is less than the distortion threshold TH_2 (e.g., Distortion Less Than Threshold?=Yes).

For example, if the navigation system 118 determines at 330-*b* that the magnitude 332-*b* of distortion (e.g., at Freq6) is less than the distortion threshold TH_2 (e.g., Distortion Less Than Threshold?=Yes), the navigation system 118 may proceed to 345. Additionally, or alternatively, the navigation system 118 may proceed to 335-*b*.

At 345, the navigation system 118 may provide navigation information 165 associated with the volume 150 and the tracking device 140 at the Freq6 in which the distortion is less than the distortion threshold TH_2 (e.g., the magnitude 332-*b* of distortion is less than the magnitude associated with the distortion threshold TH_2).

In some examples, the navigation system 118 may continue to decrease the frequency down to the frequency Freq7 at which the magnitude 332-*b* of distortion is equal to zero, and the navigation system 118 may provide navigation information 165 for the frequency range of Freq 6 through Freq 7.

Example aspects of the process flow 300 further include applying a model to further reduce the distortion. For example, even the navigation system 118 determines at 330-*b* that the distortion is below the distortion threshold TH_2 (e.g., Distortion Less Than Threshold?=Yes), the navigation system 118 may configure a model (or models) to compensate for the remaining distortion.

For example, at 335-*b*, the navigation system 118 may configure the model (or models). At 337-*b*, the navigation system 118 may apply the model to compensate for the remaining distortion. In some aspects, the navigation system 118 may store the model (or models) to the memory 106 and/or database 130. For example, the navigation system 118 may recall the model for future instances in which similar levels of distortion are determined by the navigation system 118. Accordingly, for example, the navigation system 118 may develop and apply a model that compensates for remaining distortions within the frequency range from Freq6 to Freq7.

In some alternative and/or additional aspects, the navigation system 118 may determine the frequency range spanning from Freq4 to Freq6 (e.g., from Freq4 to Freq7 and from Freq6 to Freq7) by sweeping from the relative middle of the frequency range spanning from Freq1 to Freq2. For example, the navigation system 118 may select any frequency (e.g., Freq8) in the relative middle of the frequency range spanning from Freq1 to Freq2. The navigation system 118 may determine the amount of distortion for various frequencies while sweeping from Freq8 in a direction of decreasing frequency, for example, until the distortion threshold TH_1 is reached. The navigation system 118 may determine the amount of distortion for various frequencies while sweeping from Freq8 in a direction of increasing frequency, for example, until the distortion threshold TH_2 is reached.

As described with reference to FIGS. 3A and 3B, the system 100 may support navigation with swept frequencies in association with effectively eliminating electromagnetic distortions. The system may sweep across frequencies, sense and minimizes distortions, and navigate at multiple frequencies that achieve optimal levels (e.g., below a threshold value) of coerced distortion and induced distortion. Navigation with multiple such identified frequencies may minimize distortion impacts on tracking devices 140.

In some other aspects, the system 100 may support navigation with sampled frequencies in association with effectively eliminating electromagnetic distortions. As an example, using transmission coil Tx3, the navigation system 118 may transmit a signal at Freq1, followed by transmitting the signal at Freq2, and show opposite distortions. The navigation system 118 may then, using transmission coil Tx3, transmit the signal at Freq4, followed by transmitting the signal at Freq6, followed by transmitting the signal at Freq7 (or transmitting at Freq8 and then sweeping from Freq8 to Freq7).

As another example, using transmission coil Tx3, the navigation system 118 may transmit signals at Freq1 and Freq2 simultaneously and show opposite distortions. The navigation system 118 may then, using transmission coil Tx3, transmit signals at Freq4 and Freq6 simultaneously, followed by transmitting a signal at Freq7 (or transmitting at Freq8 and sweeping to Freq7).

As another example, using transmission coil Tx3, the navigation system 118 may transmit signals at Freq1, Freq2, Freq4, and Freq6 simultaneously, followed by transmitting at Freq7 (or Freq8 and sweeping to Freq7).

According to example aspects of the present disclosure, using transmission coil Tx1 and transmission coil Tx2, the navigation system 118 may similarly sweep or sample (or sample and sweep) across the same or a slightly different set of frequencies as described herein with reference to transmission coil Tx3.

Accordingly, for example, the navigation system 118 may generate the electromagnetic field 151 at frequencies described herein to reduce distortion (e.g., coerced distortions) as magnetic permeability decreases with increasing frequency and reduce distortion (e.g., induced distortions) at low frequencies and as skin depth decreases with increasing frequency.

Figure 4:
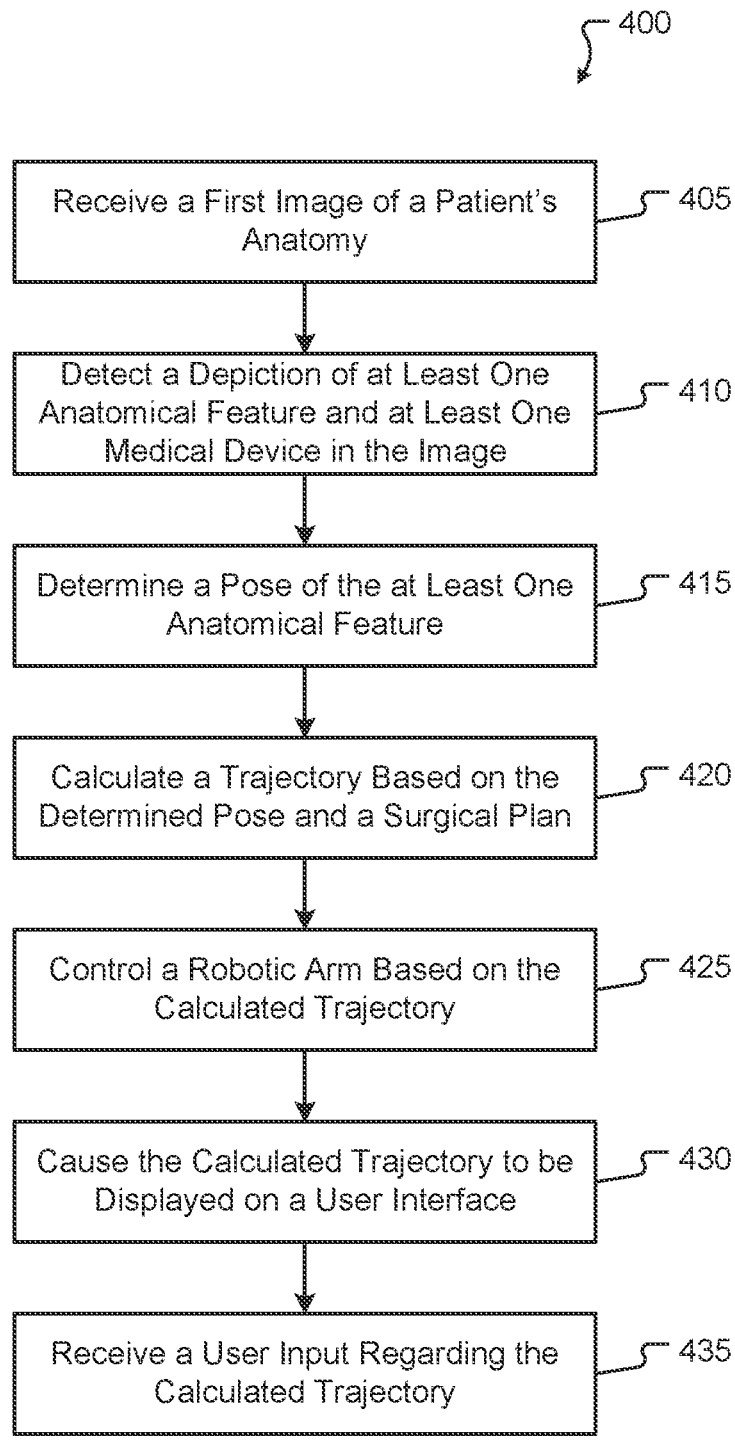
FIG. 4 illustrates an example process flow in accordance with aspects of the present disclosure.

FIG. 4 illustrates an example of a process flow 400 in accordance with aspects of the present disclosure. In some examples, process flow 400 may implement aspects of a computing device 102, an imaging device 112, a robot 114, and a navigation system 118 described with reference to FIGS. 1A and 1B.

In the following description of the process flow 400, the operations may be performed in a different order than the order shown, or the operations may be performed in different orders or at different times. Certain operations may also be left out of the process flow 400, or other operations may be added to the process flow 400. It is to be understood that any of the operations of process flow 400 may be performed by any device (e.g., a computing device 102, an imaging device 112, a robot 114, navigation system 118, etc.).

At 405, the process flow 400 includes transmitting a signal according to a set of frequencies, wherein a frequency range associated with the set of frequencies is from about 300 Hz to about 30 MHz.

At 410, the process flow 400 includes sensing an electromagnetic field based on transmitting the signal according to the set of frequencies.

At 415, the process flow 400 includes determining a distortion with respect to the set of frequencies in association with sensing the electromagnetic field.

In some aspects, determining the distortion is based on at least one of: a magnetic permeability associated with one or more objects in the environment; and a relative permeability associated with the one or more objects in the environment. In some aspects, determining the distortion includes determining at least one of: a conductive distortion associated with one or more objects in the environment; and a magnetic distortion associated with the one or more objects in the environment. In some aspects, the distortion is associated with one or more objects included in the environment, the one or more objects including at least one of: one or more ferromagnetic objects: and one or more non-ferromagnetic objects.

At 420, the process flow 400 includes identifying, from among the set of frequencies, a set of frequencies at which the magnitude of the distortion is less than the threshold value.

At 425, the process flow 400 includes configuring a model in association with the compensating for the distortion with respect to at least one frequency of the one or more frequencies.

In some aspects, the at least one frequency is greater than a threshold frequency included among the one or more frequencies.

At 430, the process flow 400 includes transmitting the signal according to one or more frequencies of the set of second frequencies.

In some aspects, transmitting the signal according to the one or more frequencies includes incrementally increasing or decreasing a frequency associated with transmitting the signal, from a first boundary frequency to a second boundary frequency included in the set of second frequencies. In some aspects, the process flow 300 may include: identifying the first boundary frequency based on a comparison of the threshold value and a first distortion magnitude associated with transmitting the signal according to the first boundary frequency; and identifying the second boundary frequency based on a comparison of the threshold value and a second distortion magnitude associated with transmitting the signal according to the second boundary frequency.

At 435, the process flow 400 includes providing navigation information associated with an environment and the tracking device in response to transmitting the signal according to the one or more frequencies, wherein the navigation information includes pose information of the tracking device.

In some aspects, providing the navigation information is based on compensating for the distortion using the model. In some aspects, compensating for the distortion using the model includes reducing a magnitude associated with the distortion.

In some aspects, the process flow 400 may include transmitting (at 405) the signal from a first transmission coil of a set of transmission coils. In some aspects, the process flow 400 may include transmitting the signal or a second signal according to one or more second frequencies of the set of frequencies, from a second transmission coil of the set of transmission coils. In some aspects, the process flow 400 may include providing the navigation information (at 435) associated with the environment and the tracking device in response to transmitting the signal or the second signal according to the one or more second frequencies.

The process flow 400 (and/or one or more operations thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also support execute the process flow 400. The at least one processor may perform operations of the process flow 400 by executing elements stored in a memory such as the memory 106. The elements stored in memory and executed by the processor may cause the processor to execute one or more operations of a function as shown in the process flow 400. One or more portions of the process flow 400 may be performed by the processor executing any of the contents of memory, such as navigation processing 129.

As noted above, the present disclosure encompasses methods with fewer than all of the steps identified in FIGS. 2A, 3A, 3B, and 4 (and the descriptions of the corresponding process flows), as well as methods that include additional steps beyond those identified in FIGS. 2A, 3A, 3B, and 4 (and the descriptions of the corresponding process flows). The present disclosure also encompasses methods that include one or more steps from one method described herein, and one or more steps from another method described herein. Any correlation described herein may be or include a registration or any other correlation.

The foregoing is not intended to limit the disclosure to the form or forms disclosed herein. In the foregoing Detailed Description, for example, various features of the disclosure are grouped together in one or more aspects, implementations, and/or configurations for the purpose of streamlining the disclosure. The features of the aspects, implementations, and/or configurations of the disclosure may be combined in alternate aspects, implementations, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, implementation, and/or configuration. Thus, the following claims are hereby incorporated into this Detailed Description, with each claim standing on its own as a separate preferred implementation of the disclosure.

Moreover, though the foregoing has included description of one or more aspects, implementations, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, implementations, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

Example aspects of the present disclosure include:

A system including: a processor; and a memory storing instructions thereon that, when executed by the processor, cause the processor to: transmit a signal according to a set of frequencies, wherein a frequency range associated with the set of frequencies is from about 300 Hz to about 30 MHz; determine a distortion in association with an electromagnetic field sensed at a tracking device, wherein the distortion is determined with respect to the set of frequencies; identify, from among the set of frequencies, a set of second frequencies at which the magnitude of the distortion is less than the threshold value; transmit the signal according to one or more frequencies of the set of second frequencies; and provide navigation information associated with an environment and the tracking device in response to transmitting the signal according to the one or more frequencies, wherein the navigation information includes pose information of the tracking device.

Any of the aspects herein, wherein the instructions are further executable by the processor to: configure a model in association with compensating for the distortion with respect to at least one frequency of the one or more frequencies, wherein providing the navigation information is based on compensating for the distortion using the model.

Any of the aspects herein, wherein compensating for the distortion using the model includes reducing the magnitude associated with the distortion.

Any of the aspects herein, wherein the at least one frequency is greater than a threshold frequency included among the one or more frequencies.

Any of the aspects herein, wherein: transmitting the signal according to the one or more frequencies includes incrementally increasing or decreasing a frequency associated with transmitting the signal, from a first boundary frequency to a second boundary frequency included in the set of second frequencies.

Any of the aspects herein, wherein: the first boundary frequency is identified based on a comparison of the threshold value and a first distortion magnitude associated with transmitting the signal according to the first boundary frequency; and the second boundary frequency is identified based on a comparison of the threshold value and a second distortion magnitude associated with transmitting the signal according to the second boundary frequency.

Any of the aspects herein, wherein determining the distortion is based on at least one of: a magnetic permeability associated with one or more objects in the environment; and a relative permeability associated with the one or more objects in the environment.

Any of the aspects herein, further including a set of transmission coils, wherein the instructions are further executable by the processor to: transmit the signal from a first transmission coil of the set of transmission coils; and transmit the signal or a second signal according to one or more second frequencies of the set of frequencies, from a second transmission coil of the set of transmission coils; and provide the navigation information associated with the environment and the tracking device in response to transmitting the signal or the second signal according to the one or more second frequencies.

Any of the aspects herein, wherein the distortion includes at least one of: a conductive distortion associated with one or more objects in the environment; and a magnetic distortion associated with the one or more objects in the environment.

Any of the aspects herein, wherein the distortion is associated with one or more objects included in the environment, the one or more objects including at least one of: one or more ferromagnetic objects: and one or more non-ferromagnetic objects.

A method including: transmitting a signal according to a set of frequencies, wherein a frequency range associated with the set of frequencies is from about 300 Hz to about 30 MHz; sensing an electromagnetic field based on transmitting the signal according to the set of frequencies; determining a distortion with respect to the set of frequencies in association with sensing the electromagnetic field; identifying, from among the set of frequencies, a set of second frequencies at which the magnitude of the distortion is less than the threshold value; transmitting the signal according to one or more frequencies of the set of second frequencies; and providing navigation information associated with an environment and the tracking device in response to transmitting the signal according to the one or more frequencies, wherein the navigation information includes pose information of the tracking device.

Any of the aspects herein, further including: configuring a model in association with the compensating for the distortion with respect to at least one frequency of the one or more frequencies, wherein providing the navigation information is based on compensating for the distortion using the model.

Any of the aspects herein, wherein compensating for the distortion using the model includes reducing a magnitude associated with the distortion.

Any of the aspects herein, wherein the at least one frequency includes a relatively high frequency included among the one or more frequencies.

Any of the aspects herein, wherein: transmitting the signal according to the one or more frequencies includes incrementally increasing or decreasing a frequency associated with transmitting the signal, from a first boundary frequency to a second boundary frequency included in the set of second frequencies.

Any of the aspects herein, further including: identifying the first boundary frequency based on a comparison of the threshold value and a first distortion magnitude associated with transmitting the signal according to the first boundary frequency; and identifying the second boundary frequency based on a comparison of the threshold value and a second distortion magnitude associated with transmitting the signal according to the second boundary frequency.

Any of the aspects herein, wherein determining the distortion is based on at least one of: a magnetic permeability associated with one or more objects in the environment; and a relative permeability associated with the one or more objects in the environment.

Any of the aspects herein, further including: transmitting the signal from a first transmission coil of a set of transmission coils; transmitting the signal or a second signal according to one or more second frequencies of the set of frequencies, from a second transmission coil of the set of transmission coils; and providing the navigation information associated with the environment and the tracking device in response to transmitting the signal or the second signal according to the one or more second frequencies.

Any of the aspects herein, wherein determining the distortion includes determining at least one of: a conductive distortion associated with one or more objects in the environment; and a magnetic distortion associated with the one or more objects in the environment.

Any of the aspects herein, wherein the distortion is associated with one or more objects included in the environment, the one or more objects including at least one of: one or more ferromagnetic objects: and one or more non-ferromagnetic objects.

A system including: a transmission device that is configured to transmit a signal according to a set of frequencies from about 300 Hz to about 30 MHz; a tracking device; a processor; and a memory storing data thereon that, when processed by the processor, cause the processor to: determine a distortion in association with an electromagnetic field sensed at the tracking device, wherein the distortion is determined with respect to the set of frequencies; identify, from among the set of frequencies, a set of second frequencies at which the magnitude of the distortion is less than the threshold value; transmit the signal using the transmission device according to one or more frequencies of the set of second frequencies; and provide navigation information associated with an environment and the tracking device in response to transmitting the signal according to the one or more frequencies, wherein the navigation information includes pose information of the tracking device.

Any of the aspects herein, wherein the data is further executable by the processor to: configure a model in association with compensating for the distortion with respect to at least one frequency of the one or more frequencies, wherein providing the navigation information is based on applying the model.

Any of the aspects herein, wherein: transmitting the signal according to the one or more frequencies includes incrementally increasing or decreasing a frequency associated with transmitting the signal, from a first boundary frequency to a second boundary frequency included in the set of second frequencies.

Any of the aspects herein, wherein: the first boundary frequency is identified based on a comparison of the threshold value and a first distortion magnitude associated with transmitting the signal according to the first boundary frequency; and the second boundary frequency is identified based on a comparison of the threshold value and a second distortion magnitude associated with transmitting the signal according to the second boundary frequency.

Any of the aspects herein, wherein determining the distortion is based on at least one of: a magnetic permeability associated with one or more objects in the environment; and a relative permeability associated with the one or more objects in the environment.

Any of the aspects herein, wherein the transmission device includes a set of transmission coils, and the data is further executable by the processor to: transmit the signal from a first transmission coil of the set of transmission coils; transmit the signal or a second signal according to one or more second frequencies of the set of frequencies, from a second transmission coil of the set of transmission coils; and provide the navigation information associated with the environment and the tracking device in response to transmitting the signal or the second signal according to the one or more second frequencies.

Any of the aspects herein, wherein the distortion includes at least one of: a conductive distortion associated with one or more objects in the environment; and a magnetic distortion associated with the one or more objects in the environment.

Any of the aspects herein, wherein the distortion is associated with one or more objects included in the environment, the one or more objects including at least one of: one or more ferromagnetic objects: and one or more non-ferromagnetic objects.

A system, including: navigation circuitry to provide navigation information associated with an environment by: transmitting a signal according to a set of frequencies, wherein a frequency range associated with the set of frequencies is from about 300 Hz to about 30 MHz; sensing an electromagnetic field based on transmitting the signal according to the set of frequencies; determining a distortion in association with sensing the electromagnetic field, wherein the distortion is determined with respect to the set of frequencies; identifying, from among the set of frequencies, a set of second frequencies at which the magnitude of the distortion is less than the threshold value; transmitting the signal according to one or more frequencies of the set of second frequencies; and providing navigation information associated with an environment in response to transmitting the signal according to the one or more frequencies, wherein the navigation information includes pose information of one or more objects in the environment.

A non-transitory computer readable medium including instructions, which when executed by a processor: transmits a signal according to a set of frequencies, wherein a frequency range associated with the set of frequencies is from about 300 Hz to about 30 MHz; determines a distortion in association with an electromagnetic field sensed at a tracking device, wherein the distortion is determined with respect to the set of frequencies; identifies, from among the set of frequencies, a set of second frequencies at which a magnitude of the distortion is less than the threshold value; transmits the signal according to one or more frequencies of the set of second frequencies; and provides navigation information associated with an environment and the tracking device in response to transmitting the signal according to the one or more frequencies, wherein the navigation information includes pose information of the tracking device.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/implementations in combination with any one or more other aspects/features/implementations.

Use of any one or more of the aspects or features as disclosed herein.

It is to be appreciated that any feature described herein can be claimed in combination with any other feature(s) as described herein, regardless of whether the features come from the same described implementation.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an implementation that is entirely hardware, an implementation that is entirely software (including firmware, resident software, micro-code, etc.) or an implementation combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

What is claimed is:

1. A system comprising:
   a processor; and
   a memory storing instructions thereon that, when executed by the processor, cause the processor to:
     transmit, to at least one of a tracking device and one or more objects in an environment, a signal according to a set of frequencies, wherein a frequency range associated with the set of frequencies is from about 300 Hz to about 30 MHz;
     determine a distortion in association with an electromagnetic field sensed at the tracking device, wherein the distortion is determined with respect to the set of frequencies, and wherein the distortion is based at least one a relative permeability associated with the one or more objects in the environment;
     identify, from among the set of frequencies, a set of second frequencies at which a magnitude of the relative permeability associated with the one or more objects is less than a threshold value;
     transmit, to at least one of the tracking device and the one or more objects in the environment, the signal according to one or more frequencies of the set of second frequencies; and
     provide navigation information associated with the environment and the tracking device in response to transmitting the signal according to the one or more frequencies, wherein the navigation information comprises pose information of the tracking device.

2. The system of claim 1, wherein the instructions are further executable by the processor to:
   configure a model in association with compensating for the distortion with respect to at least one frequency of the one or more frequencies,
   wherein providing the navigation information is based on compensating for the distortion using the model.

3. The system of claim 2, wherein compensating for the distortion using the model comprises reducing a magnitude associated with the distortion.

4. The system of claim 2, wherein the at least one frequency is greater than a threshold frequency included among the one or more frequencies, wherein the threshold frequency is equal to or greater than a minimum frequency of the one or more frequencies, and wherein the threshold frequency is less than a maximum frequency of the one or more frequencies.

5. The system of claim 1, wherein:
   transmitting the signal according to the one or more frequencies comprises incrementally increasing or decreasing a frequency associated with transmitting the signal, from a first boundary frequency to a second boundary frequency included in the set of second frequencies.

6. The system of claim 1, wherein determining the distortion is further based on:
   a magnetic permeability associated with one or more objects in the environment.

7. The system of claim 1, further comprising a set of transmission coils, wherein the instructions are further executable by the processor to:
   transmit the signal from a first transmission coil of the set of transmission coils;
   transmit the signal or a second signal according to one or more second frequencies of the set of frequencies, from a second transmission coil of the set of transmission coils; and
   provide the navigation information associated with the environment and the tracking device in response to transmitting the signal or the second signal according to the one or more second frequencies.

8. The system of claim 1, wherein the distortion comprises at least one of:
   a conductive distortion associated with one or more objects in the environment; and
   a magnetic distortion associated with the one or more objects in the environment.

9. The system of claim 1, wherein the one or more objects comprise at least one of:
   one or more ferromagnetic objects: and
   one or more non-ferromagnetic objects.

10. A method comprising:
    transmitting, by a processor and to at least one of a tracking device and one or more objects in an environment, a signal according to a set of frequencies, wherein a frequency range associated with the set of frequencies is from about 300 Hz to about 30 MHz;

receiving, by the processing, sensed information associated with an electromagnetic field based on transmitting the signal according to the set of frequencies;

determining, by the processor, a distortion with respect to the set of frequencies in association with sensing the electromagnetic field, wherein the distortion is based at least on a relative permeability with the one or more objects in the environment;

identifying, from among the set of frequencies and by the processor, a set of second frequencies at which the magnitude of the relative permeability associated with the one or more objects is less than the threshold value;

transmitting, by the processor and to at least one of the tracking device and the one or more objects in the environment, the signal according to one or more frequencies of the set of second frequencies; and providing, by the processor, navigation information associated with the environment and the tracking device in response to transmitting the signal according to the one or more frequencies, wherein the navigation information comprises pose information of the tracking device.

11. The method of claim 10, further comprising:
configuring a model in association with the compensating for the distortion with respect to at least one frequency of the one or more frequencies,
wherein providing the navigation information is based on compensating for the distortion using the model.

12. The method of claim 11, wherein compensating for the distortion using the model comprises reducing a magnitude associated with the distortion.

13. The method of claim 11, wherein the at least one frequency comprises a first frequency included among the one or more frequencies, wherein the first frequency is greater than or equal to a median frequency of the one or more frequencies, and wherein the first frequency is less than a maximum frequency of the one or more frequencies.

14. The method of claim 10, wherein:
transmitting the signal according to the one or more frequencies comprises incrementally increasing or decreasing a frequency associated with transmitting the signal, from a first boundary frequency to a second boundary frequency included in the set of second frequencies.

15. The method of claim 10, wherein determining the distortion is based on:
a magnetic permeability associated with one or more objects in the environment.

16. The method of claim 10, further comprising:
transmitting the signal from a first transmission coil of a set of transmission coils;
transmitting the signal or a second signal according to one or more second frequencies of the set of frequencies, from a second transmission coil of the set of transmission coils; and
providing the navigation information associated with the environment and the tracking device in response to transmitting the signal or the second signal according to the one or more second frequencies.

17. The method of claim 10, wherein determining the distortion comprises determining at least one of:
a conductive distortion associated with one or more objects in the environment; and
a magnetic distortion associated with the one or more objects in the environment.

18. The method of claim 10, wherein the one or more objects comprise at least one of:
one or more ferromagnetic objects: and
one or more non-ferromagnetic objects.

19. A system comprising:
a transmission device that is configured to transmit a signal according to a set of frequencies from about 300 Hz to about 30 MHz;
a tracking device;
a processor; and
a memory storing data thereon that, when processed by the processor, cause the processor to:
determine a distortion in association with an electromagnetic field sensed at the tracking device, wherein the distortion is determined with respect to the set of frequencies, and wherein the distortion is based at least on a relative permeability associated with one or more objects in an environment;
identify, from among the set of frequencies, a set of second frequencies at which a magnitude of the relative permeability associated with the one or more objects is less than a threshold value;
transmit, to at least one of the tracking device and the one or more objects in the environment, the signal using the transmission device according to one or more frequencies of the set of second frequencies; and
provide navigation information associated with the environment and the tracking device in response to transmitting the signal according to the one or more frequencies, wherein the navigation information comprises pose information of the tracking device.

20. The system of claim 19, wherein the data is further executable by the processor to:
configure a model in association with compensating for the distortion with respect to at least one frequency of the one or more frequencies,
wherein providing the navigation information is based on applying the model.

21. The system of claim 19, wherein:
transmitting the signal according to the one or more frequencies comprises incrementally increasing or decreasing a frequency associated with transmitting the signal, from a first boundary frequency to a second boundary frequency included in the set of second frequencies.

22. The system of claim 19, wherein determining the distortion is further based on:
a magnetic permeability associated with one or more objects in the environment.

23. The system of claim 19, wherein the transmission device comprises a set of transmission coils, and the data is further executable by the processor to:
transmit the signal from a first transmission coil of the set of transmission coils;
transmit the signal or a second signal according to one or more second frequencies of the set of frequencies, from a second transmission coil of the set of transmission coils; and
provide the navigation information associated with the environment and the tracking device in response to transmitting the signal or the second signal according to the one or more second frequencies.

24. The system of claim 19, wherein the distortion comprises at least one of:
a conductive distortion associated with one or more objects in the environment; and a magnetic distortion associated with the one or more objects in the environment.

25. The system of claim 19, wherein the one or more objects comprise at least one of:
   one or more ferromagnetic objects: and
   one or more non-ferromagnetic objects.

26. A system, comprising:
   navigation circuitry to provide navigation information associated with an environment by:
      transmitting, to at least one of a tracking device and one or more objects in the environment, a signal according to a set of frequencies, wherein a frequency range associated with the set of frequencies is from about 300 Hz to 30 MHz;
      sensing an electromagnetic field based on transmitting the signal according to the set of frequencies;
      determining a distortion in association with sensing the electromagnetic field, wherein the distortion is determined with respect to the set of frequencies, and wherein the distortion is based at least on a relative permeability associated with the one or more objects in the environment;
      identifying, from among the set of frequencies, a set of second frequencies at which a magnitude of the relative permeability associated with the one or more object is less than than a threshold value;
      transmitting, to at least one of the tracking device and the one or more objects in the environment, the signal according to one or more frequencies of the set of second frequencies; and
      providing the navigation information associated with the environment in response to transmitting the signal according to the one or more frequencies, wherein the navigation information comprises pose information of the one or more objects in the environment.

27. A non-transitory computer readable medium comprising instructions, which when executed by a processor:
   transmits, to at least one of a tracking device and one or more objects in an environment, a signal according to a set of frequencies, wherein a frequency range associated with the set of frequencies is from about 300 Hz to 30 MHz;
   determines a distortion in association with an electromagnetic field sensed at the tracking device, wherein the distortion is determined with respect to the set of frequencies, and wherein the distortion is based on at least on a relative permeability associated with the one or more objects in the environment;
   identifies, from among the set of frequencies, a set of second frequencies at which a magnitude of the relative permeability associated with the one or more objects is less than a threshold value;
   transmits, to at least one of the tracking device and the one or more objects in the environment, the signal according to one or more frequencies of the set of second frequencies; and
   provides navigation information associated with the environment and the tracking device in response to transmitting the signal according to the one or more frequencies, wherein the navigation information comprises pose information of the tracking device.

28. The system of claim 1, wherein the relative permeability is determined based on a ratio of magnetic permeability and a permeability of free space.

29. The system of claim 1, wherein the navigation information is used by a navigation system to manipulate a surgical tool relative to the tracking device.

30. The method of claim 10, wherein the relative permeability is determined based on a ratio of magnetic permeability and a permeability of free space.

* * * * *